(12) United States Patent
Reinecke et al.

(10) Patent No.: US 8,980,594 B2
(45) Date of Patent: Mar. 17, 2015

(54) USE OF A PROTEIN HOMOLOGOUS TO A MEAB PROTEIN FOR INCREASING THE ENZYMATIC ACTIVITY OF A 3-HYDROXYCARBOXYLIC ACID-COA MUTASE

(75) Inventors: Liv Reinecke, Essen (DE); Steffen Schaffer, Herten (DE); Tim Koehler, Dorsten (DE); Anja Thiessenhusen, Muenster (DE); Achim Marx, Gelnhausen (DE); Markus Buchhaupt, Bad Vilbel (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 13/500,041

(22) PCT Filed: Oct. 11, 2010

(86) PCT No.: PCT/EP2010/065151
§ 371 (c)(1),
(2), (4) Date: Apr. 3, 2012

(87) PCT Pub. No.: WO2011/057871
PCT Pub. Date: May 19, 2011

(65) Prior Publication Data
US 2012/0264182 A1    Oct. 18, 2012

(30) Foreign Application Priority Data

Nov. 11, 2009 (DE) .......................... 10 2009 046 623

(51) Int. Cl.
| | |
|---|---|
| *C12P 7/42* | (2006.01) |
| *C12P 7/40* | (2006.01) |
| *C12P 7/62* | (2006.01) |
| *C12N 9/90* | (2006.01) |
| *C12N 9/14* | (2006.01) |
| *C12P 7/52* | (2006.01) |
| *C07K 14/195* | (2006.01) |

(52) U.S. Cl.
CPC .................. *C12P 7/52* (2013.01); *C07K 14/195* (2013.01); *C12N 9/90* (2013.01); *C12P 7/42* (2013.01); *C07K 2319/00* (2013.01)
USPC ........... 435/146; 435/136; 435/135; 435/233; 435/195

(58) Field of Classification Search
None
See application file for complete search history.

(56) References Cited

U.S. PATENT DOCUMENTS

| | | | |
|---|---|---|---|
| 7,923,225 B2 | 4/2011 | Mueller et al. |
| 8,372,595 B2 | 2/2013 | Schaffer et al. |
| 8,604,227 B2 | 12/2013 | Petrat et al. |
| 2009/0075281 A1 | 3/2009 | Hristova et al. |
| 2010/0021977 A1 | 1/2010 | May et al. |
| 2010/0068773 A1 | 3/2010 | Marx et al. |
| 2010/0190224 A1 | 7/2010 | Poetter et al. |
| 2010/0261237 A1 | 10/2010 | Verseck et al. |
| 2010/0291644 A1 | 11/2010 | Marx et al. |
| 2010/0323418 A1 | 12/2010 | Burgard |
| 2010/0324257 A1 | 12/2010 | Karau et al. |
| 2011/0039313 A1 | 2/2011 | Verseck et al. |
| 2011/0118433 A1 | 5/2011 | Pötter et al. |
| 2011/0118504 A1 | 5/2011 | Haas et al. |
| 2011/0171702 A1 | 7/2011 | Reinecke et al. |
| 2011/0189742 A1 | 8/2011 | Haas et al. |
| 2011/0257429 A1 | 10/2011 | Schraven et al. |
| 2012/0034665 A1 | 2/2012 | Haas et al. |
| 2012/0041216 A1 | 2/2012 | Sieber et al. |
| 2012/0245375 A1 | 9/2012 | Hannen et al. |
| 2013/0035403 A1 | 2/2013 | Schaffer et al. |
| 2013/0052700 A1 | 2/2013 | Poetter et al. |
| 2013/0092233 A1 | 4/2013 | Pawlik et al. |
| 2013/0130319 A1 | 5/2013 | Schaffer et al. |
| 2013/0165672 A1 | 6/2013 | Klasovsky et al. |
| 2013/0165685 A1 | 6/2013 | Hannen et al. |
| 2013/0183725 A1 | 7/2013 | Poetter et al. |
| 2013/0245276 A1 | 9/2013 | Klasovsky et al. |
| 2013/0331580 A1 | 12/2013 | Klasovsky et al. |

FOREIGN PATENT DOCUMENTS

| | | |
|---|---|---|
| DE | 10 2008 002 715 | 12/2009 |
| WO | WO 2007/110394 A2 | 10/2007 |
| WO | 2010 127303 | 11/2010 |
| WO | 2011 036000 | 3/2011 |
| WO | 2011 157573 | 12/2011 |

OTHER PUBLICATIONS

Yaneva et al., J. Biol. Chem. 287:15502-15511, 2012.*
GenBank Accession No. JQ708092, Jun. 2012, 4 pages.*
Korotkova, N., et al., "MeaB and MeaD are Newly Identified Enzymes Involved in the Interconversion of Methylmalonyl-CoA and Succinyl-CoA," American Society for Microbiology 103rd General Meeting, vol. 103, XP-009149172, (May 21, 2003).
Korotkova, N., et al., "MeaB Is a Component of the Methylmalonyl-CoA Mutase Complex Required for Protection of the Enzyme from Inactivation," Journal of Biological Chemistry, American Society for Biochemistry and Molecular Biology Inc., vol. 279, No. 14, pp. 13652-13658, XP-002642432, (Apr. 2, 2004).
Rohwerder, T., et al., "The Alkyl tert-Butyl Ether Intermediate 2-Hydroxyisobutyrate Is Degraded via a Novel Cobalamin-Dependent Mutase Pathway," Applied and Environmental Microbiology, American Society for Microbiology, vol. 72, No. 6, pp. 4128-4135, XP-002460829, (Jun. 2006).

(Continued)

*Primary Examiner* — David J Steadman
(74) *Attorney, Agent, or Firm* — Oblon, McClelland, Maier & Neustadt, L.L.P.

(57) ABSTRACT

The invention relates to the use of a protein homologous to a MeaB protein for increasing the enzymatic activity of a 3-hydroxycarboxylic acid-CoA mutase, a fusion protein comprising a 3-hydroxycarboxylic acid-CoA mutase and a protein sequence homologous to a MeaB protein and an enzymatic method for producing 2-hydroxyisobutyric acid.

15 Claims, 6 Drawing Sheets

(56) References Cited

OTHER PUBLICATIONS

Reeves, A.R., et al., "Engineering of the methylmalonyl-CoA metabolite node of Saccharopolyspora erythraea for increased erythromycin production," Metabolic Engineering, Elsevier, vol. 9, No. 3, pp. 293-303, XP-025322491, (May 1, 2007).

Polley, S.D., et al., "Molecular characterisation of meaB, a novel gene affecting nitrogen metabolite repression in Aspergillus nidulans," FEBS Letters, vol. 388, No. 2-3, pp. 200-205, XP-002155630, (1996).

Rohwerder, T., et al., "Biosynthesis of 2-hydroxyisobutyric acid (2-HIBA) from renewable carbon", Microbial Cell Factories, BioMed Central, vol. 9, Total 10 Pages, XP-021067683, (Feb. 25, 2010).

Cracan, V., et al., "IcmF Is a Fusion between the Radical $B_{12}$ Enzyme Isobutyryl-CoA Mutase and Its G-protein Chaperone," The Journal of Biological Chemistry, vol. 285, No. 1, pp. 655-666, XP-002642434, (Jan. 1, 2010).

International Search Report Issued on Oct. 17, 2011 in PCT/EP10/65151 Filed on Oct. 11, 2010.

Search Report issued Mar. 7, 2011 in German Application No. 10 2009 046 623.1 (With English Translation of Category of Cited Documents).

Combined Office Action and Search Report issued Aug. 27, 2013 in Chinese Application No. 201080051033.9.

Staci R. Kane, et al., "Whole-Genome Analysis of the Methyl *tert*-Butyl Ether-Degrading Beta-Proteobacterium *Methylibium petroleiphilum* PM1", Journal of Bacteriology, vol. 189, No. 5, Mar. 2007, pp. 1931-1945.

Ute Lechner, et al., "*Aquincola tertiaricarbonis* gen. nov., sp. nov., a *tertiary* butyl moiety-degrading bacterium", International Journal of Systematic and Evolutionary Microbiology, vol. 57, 2007, pp. 1295-1303.

"Putative transport system kinase [*Methylibium petroleiphilum* PM1]", Genbank-Eintrag, Accession No. YP_001023545, Apr. 29, 2009, 2 pages.

U.S. Appl. No. 14/126,607, filed Dec. 16, 2013, Haas, et al.
U.S. Appl. No. 14/233,505, filed Jan. 17, 2014, Poetter, et al.
U.S. Appl. No. 14/237,121, filed Feb. 4, 2014, Haas, et al.
U.S. Appl. No. 14/238,576, filed Feb. 12, 2014, Schaffer, et al.
U.S. Appl. No. 14/238,591, filed Feb. 12, 2014, Schaffer, et al.

\* cited by examiner

US 8,980,594 B2

SEQUENCE LISTING

```
<160> NUMBER OF SEQ ID NOS: 29

<210> SEQ ID NO 1
<211> LENGTH: 327
<212> TYPE: PRT
<213> ORGANISM: Aquincola tertiaricarbonis

<400> SEQUENCE: 1

Met Thr Tyr Val Pro Ser Ser Ala Leu Leu Glu Gln Leu Arg Ala Gly
1               5                   10                  15

Asn Thr Trp Ala Leu Gly Arg Leu Ile Ser Arg Ala Glu Ala Gly Val
            20                  25                  30

Ala Glu Ala Arg Pro Ala Leu Ala Glu Val Tyr Arg His Ala Gly Ser
        35                  40                  45

Ala His Val Ile Gly Leu Thr Gly Val Pro Gly Ser Gly Lys Ser Thr
    50                  55                  60

Leu Val Ala Lys Leu Thr Ala Ala Leu Arg Lys Arg Gly Glu Lys Val
65                  70                  75                  80

Gly Ile Val Ala Ile Asp Pro Ser Ser Pro Tyr Ser Gly Gly Ala Ile
                85                  90                  95

Leu Gly Asp Arg Ile Arg Met Thr Glu Leu Ala Asn Asp Ser Gly Val
            100                 105                 110

Phe Ile Arg Ser Met Ala Thr Arg Gly Ala Thr Gly Gly Met Ala Arg
        115                 120                 125

Ala Ala Leu Asp Ala Val Asp Leu Leu Asp Val Ala Gly Tyr His Thr
    130                 135                 140

Ile Ile Leu Glu Thr Val Gly Val Gly Gln Asp Glu Val Glu Val Ala
145                 150                 155                 160

His Ala Ser Asp Thr Thr Val Val Ser Ala Pro Gly Leu Gly Asp Asp
                165                 170                 175

Glu Ile Gln Ala Ile Lys Ala Gly Val Leu Glu Ile Ala Asp Ile His
            180                 185                 190

Val Val Ser Lys Cys Asp Arg Asp Asp Ala Asn Arg Thr Leu Thr Asp
        195                 200                 205

Leu Lys Gln Met Leu Thr Leu Gly Thr Met Val Gly Pro Lys Arg Ala
    210                 215                 220

Trp Ala Ile Pro Val Val Gly Val Ser Ser Tyr Thr Gly Glu Gly Val
225                 230                 235                 240
```

Asp Asp Leu Leu Gly Arg Ile Ala Ala His Arg Gln Ala Thr Ala Asp
            245                 250                 255

Thr Glu Leu Gly Arg Glu Arg Arg Arg Val Ala Glu Phe Arg Leu
        260                 265                 270

Gln Lys Thr Ala Glu Thr Leu Leu Glu Arg Phe Thr Thr Gly Ala
        275                 280                 285

Gln Pro Phe Ser Pro Ala Leu Ala Asp Ser Leu Ser Asn Arg Ala Ser
        290                 295                 300

Asp Pro Tyr Ala Ala Ala Arg Glu Leu Ile Ala Arg Thr Ile Arg Lys
305                 310                 315                 320

Glu Tyr Ser Asn Asp Leu Ala
            325

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 2

Cys Ala Gly Ser Phe Pro Thr Ile
1               5

<210> SEQ ID NO 3
<211> LENGTH: 894
<212> TYPE: PRT
<213> ORGANISM: Aquincola tertiaricarbonis

<400> SEQUENCE: 3

Met Thr Tyr Val Pro Ser Ser Ala Leu Leu Glu Gln Leu Arg Ala Gly
1               5                   10                  15

Asn Thr Trp Ala Leu Gly Arg Leu Ile Ser Arg Ala Glu Ala Gly Val
            20                  25                  30

Ala Glu Ala Arg Pro Ala Leu Ala Glu Val Tyr Arg His Ala Gly Ser
        35                  40                  45

Ala His Val Ile Gly Leu Thr Gly Val Pro Gly Ser Gly Lys Ser Thr
    50                  55                  60

Leu Val Ala Lys Leu Thr Ala Ala Leu Arg Lys Arg Gly Glu Lys Val
65                  70                  75                  80

Gly Ile Val Ala Ile Asp Pro Ser Ser Pro Tyr Ser Gly Gly Ala Ile
                85                  90                  95

Leu Gly Asp Arg Ile Arg Met Thr Glu Leu Ala Asn Asp Ser Gly Val
            100                 105                 110

Phe Ile Arg Ser Met Ala Thr Arg Gly Ala Thr Gly Gly Met Ala Arg
        115                 120                 125

Ala Ala Leu Asp Ala Val Asp Leu Leu Asp Val Ala Gly Tyr His Thr
    130                 135                 140

Ile Ile Leu Glu Thr Val Gly Val Gly Gln Asp Glu Val Glu Val Ala
145                 150                 155                 160

His Ala Ser Asp Thr Thr Val Val Val Ser Ala Pro Gly Leu Gly Asp
                165                 170                 175

Glu Ile Gln Ala Ile Lys Ala Gly Val Leu Glu Ile Ala Asp Ile His
            180                 185                 190

Val Val Ser Lys Cys Asp Arg Asp Asp Ala Asn Arg Thr Leu Thr Asp
        195                 200                 205

```
Leu Lys Gln Met Leu Thr Leu Gly Thr Met Val Gly Pro Lys Arg Ala
    210                 215                 220

Trp Ala Ile Pro Val Val Gly Val Ser Ser Tyr Thr Gly Glu Gly Val
225                 230                 235                 240

Asp Asp Leu Leu Gly Arg Ile Ala Ala His Arg Gln Ala Thr Ala Asp
                245                 250                 255

Thr Glu Leu Gly Arg Glu Arg Arg Arg Val Ala Glu Phe Arg Leu
        260                 265                 270

Gln Lys Thr Ala Glu Thr Leu Leu Glu Arg Phe Thr Thr Gly Ala
            275                 280                 285

Gln Pro Phe Ser Pro Ala Leu Ala Asp Ser Leu Ser Asn Arg Ala Ser
290                 295                 300

Asp Pro Tyr Ala Ala Arg Glu Leu Ile Ala Arg Thr Ile Arg Lys
305                 310                 315                 320

Glu Tyr Ser Asn Asp Leu Ala Cys Ala Lys Leu Thr Ile Thr Trp Leu
                325                 330                 335

Glu Pro Gln Ile Lys Ser Gln Leu Gln Ser Glu Arg Lys Asp Trp Glu
            340                 345                 350

Ala Asn Glu Val Gly Ala Phe Leu Lys Lys Ala Pro Glu Arg Lys Glu
            355                 360                 365

Gln Phe His Thr Ile Gly Asp Phe Pro Val Gln Arg Thr Tyr Thr Ala
    370                 375                 380

Ala Asp Ile Ala Asp Thr Pro Leu Glu Asp Ile Gly Leu Pro Gly Arg
385                 390                 395                 400

Tyr Pro Phe Thr Arg Gly Pro Tyr Pro Thr Met Tyr Arg Ser Arg Thr
                405                 410                 415

Trp Thr Met Arg Gln Ile Ala Gly Phe Gly Thr Gly Glu Asp Thr Asn
            420                 425                 430

Lys Arg Phe Lys Tyr Leu Ile Ala Gln Gly Gln Thr Gly Ile Ser Thr
        435                 440                 445

Asp Phe Asp Met Pro Thr Leu Met Gly Tyr Asp Ser Asp His Pro Met
    450                 455                 460

Ser Asp Gly Glu Val Gly Arg Glu Gly Val Ala Ile Asp Thr Leu Ala
465                 470                 475                 480

Asp Met Glu Ala Leu Leu Ala Asp Ile Asp Leu Glu Lys Ile Ser Val
                485                 490                 495

Ser Phe Thr Ile Asn Pro Ser Ala Trp Ile Leu Leu Ala Met Tyr Val
            500                 505                 510

Ala Leu Gly Glu Lys Arg Gly Tyr Asp Leu Asn Lys Leu Ser Gly Thr
            515                 520                 525

Val Gln Ala Asp Ile Leu Lys Glu Tyr Met Ala Gln Lys Glu Tyr Ile
    530                 535                 540

Tyr Pro Ile Ala Pro Ser Val Arg Ile Val Arg Asp Ile Ile Thr Tyr
545                 550                 555                 560

Ser Ala Lys Asn Leu Lys Arg Tyr Asn Pro Ile Asn Ile Ser Gly Tyr
                565                 570                 575

His Ile Ser Glu Ala Gly Ser Ser Pro Leu Gln Glu Ala Ala Phe Thr
            580                 585                 590

Leu Ala Asn Leu Ile Thr Tyr Val Asn Glu Val Thr Lys Thr Gly Met
            595                 600                 605

His Val Asp Glu Phe Ala Pro Arg Leu Ala Phe Phe Val Ser Gln
    610                 615                 620

Gly Asp Phe Phe Glu Glu Val Ala Lys Phe Arg Ala Leu Arg Arg Cys
```

```
                625                 630                 635                 640
Tyr Ala Lys Ile Met Lys Glu Arg Phe Gly Ala Arg Asn Pro Glu Ser
                    645                 650                 655
Met Arg Leu Arg Phe His Cys Gln Thr Ala Ala Ala Thr Leu Thr Lys
                660                 665                 670
Pro Gln Tyr Met Val Asn Val Arg Thr Ser Leu Gln Ala Leu Ser
            675                 680                 685
Ala Val Leu Gly Gly Ala Gln Ser Leu His Thr Asn Gly Tyr Asp Glu
    690                 695                 700
Ala Phe Ala Ile Pro Thr Glu Asp Ala Met Lys Met Ala Leu Arg Thr
705                 710                 715                 720
Gln Gln Ile Ile Ala Glu Glu Ser Gly Val Ala Asp Val Ile Asp Pro
                    725                 730                 735
Leu Gly Gly Ser Tyr Tyr Val Glu Ala Leu Thr Thr Glu Tyr Glu Lys
                740                 745                 750
Lys Ile Phe Glu Ile Leu Glu Glu Val Glu Lys Arg Gly Gly Thr Ile
            755                 760                 765
Lys Leu Ile Glu Gln Gly Trp Phe Gln Lys Gln Ile Ala Asp Phe Ala
    770                 775                 780
Tyr Glu Thr Ala Leu Arg Lys Gln Ser Gly Gln Lys Pro Val Ile Gly
785                 790                 795                 800
Val Asn Arg Phe Val Glu Asn Glu Glu Asp Val Lys Ile Glu Ile His
                    805                 810                 815
Pro Tyr Asp Asn Thr Thr Ala Glu Arg Gln Ile Ser Arg Thr Arg Arg
                820                 825                 830
Val Arg Ala Glu Arg Asp Glu Ala Lys Val Gln Ala Met Leu Asp Gln
            835                 840                 845
Leu Val Ala Val Ala Lys Asp Glu Ser Gln Asn Leu Met Pro Leu Thr
    850                 855                 860
Ile Glu Leu Val Lys Ala Gly Ala Thr Met Gly Asp Ile Val Glu Lys
865                 870                 875                 880
Leu Lys Gly Ile Trp Gly Thr Tyr Arg Glu Thr Pro Val Phe
                    885                 890

<210> SEQ ID NO 4
<211> LENGTH: 136
<212> TYPE: PRT
<213> ORGANISM: Aquincola tertiaricarbonis

<400> SEQUENCE: 4

Met Asp Gln Thr Pro Ile Arg Val Leu Leu Ala Lys Val Gly Leu Asp
1               5                   10                  15
Gly His Asp Arg Gly Val Lys Val Val Ala Arg Ala Leu Arg Asp Ala
                20                  25                  30
Gly Met Asp Val Ile Tyr Ser Gly Leu His Arg Thr Pro Glu Glu Val
            35                  40                  45
Val Asn Thr Ala Ile Gln Glu Asp Val Asp Val Leu Gly Val Ser Leu
    50                  55                  60
Leu Ser Gly Val Gln Leu Thr Val Phe Pro Lys Ile Phe Lys Leu Leu
65                  70                  75                  80
Asp Glu Arg Gly Ala Gly Asp Leu Ile Val Ile Ala Gly Gly Val Met
                85                  90                  95
Pro Asp Glu Asp Ala Ala Ala Ile Arg Lys Leu Gly Val Arg Glu Val
                100                 105                 110
```

```
Leu Leu Gln Asp Thr Pro Pro Gln Ala Ile Ile Asp Ser Ile Arg Ser
    115                 120                 125

Leu Val Ala Ala Arg Gly Ala Arg
    130             135

<210> SEQ ID NO 5
<211> LENGTH: 2685
<212> TYPE: DNA
<213> ORGANISM: Aquincola tertiaricarbonis

<400> SEQUENCE: 5
atgacttacg ttccctcatc cgccttgctc gagcaactcc gagccggcaa tacctgggcg      60
cttggccgcc tgatctcgcg cgccgaggcc ggtgtggccg aggcgcggcc agcattggcc     120
gaggtctatc ggcacgccgg ctcggcgcat gtgatcggtc tcaccggggt gccggggagt     180
ggcaagtcga ctctcgtggc gaagctcacg gccgccctgc gcaagcgtgg tgaaaaggtc     240
ggcatcgtcg caatcgatcc gtcgagcccg tactcgggcg gtgcgatcct cggcgaccgt     300
atccgaatga ccgaactcgc caacgattcc ggcgtattca tccgcagcat ggccacgcgc     360
ggcgcgacgg ggggcatggc gcgtgccgcc ctcgacgccg tggacctgct ggatgtcgcc     420
ggctatcaca ccatcatcct ggagactgtc ggagtcggtc aggacgaggt ggaggtggcg     480
cacgcatcgg acacgacagt cgtcgtatcg gcgccaggcc ttggagacga gatccaggcc     540
atcaaagccg gcgtcctgga aatcgccgac atccatgttg tcagcaagtg tgaccgcgac     600
gacgcgaatc gcacgctcac cgatctcaag cagatgctga cgctcggcac catggtcggg     660
cccaagcgcg catgggcgat cccggtcgtc ggtgtcagtt cgtacacagg cgaaggcgtc     720
gacgacctgc tcggtcgcat cgccgcccac cgccaggcga cggccgacac cgaactcggc     780
cgcgaacggc gccgtcgcgt agccgaattc gccttcagag agaccgccga cgcgctgctc     840
ctggagcgat tcaccaccgg agcgcagccc ttctcgcctg cgctcgcaga cagcctcagc     900
aaccgtgcgt cggatcccta cgccgcagca cgcgaactca tcgcccgaac gatccgcaag     960
gagtactcga atgacctggc ttgcgccaag cttaccataa cctggcttga gccgcagata    1020
aagtcccaac tccaatcgga gcgcaaggac tgggaagcga acgaagtcgg cgccttcttg    1080
aagaaggcgc ccgagcgcaa ggagcagttc cacacgatcg gggacttccc ggtccagcgc    1140
acctacaccg ctgccgacat cgccgacacg ccgctggagg acatcggtct tccggggcgc    1200
tacccgttca cgcgcgggcc ctacccgacg atgtaccgca gccgcacctg gacgatgcgc    1260
cagatcgccg gcttcggcac cggcgaggac accaacaagc gcttcaagta tctgatcgcg    1320
cagggccaga ccggcatctc caccgacttc gacatgccca cgctgatggg ctacgactcc    1380 gaccaccccga tgagcgacgg cgaggtcggc gcgagggcg tggcgatcga cacgctggcc    1440
gacatggagg cgctgctggc cgacatcgac ctcgagaaga tctcggtctc gttcacgatc    1500
aacccgagcg cctggatcct gctcgcgatg tacgtggcgc tcggcgagaa gcgcggctac    1560
gacctgaaca agctgtcggg cacgtgcag gccgacatcc tgaaggagta catggcgcag    1620
aaggagtaca tctacccgat cgcgccgtcg gtgcgcatcg tgcgcgacat catcacctac    1680
agcgcgaaga acctgaagcg ctacaacccg atcaacatct cgggctacca catcagcgag    1740
gccggctcct cgccgctcca ggaggcggcc ttcacgctgg ccaacctgat cacctacgtg    1800
aacgaggtga cgaagaccgg tatgcacgtc gacgaattcg cgccgcggtt ggccttcttc    1860
ttcgtgtcgc aaggtgactt cttcgaggag gtcgcgaagt ccgcgccct cgccgctgc    1920 tacgcgaaga tcatgaagga gcgcttcggt gcaagaaatc cggaatcgat gcggttgcgc    1980
```

```
ttccactgtc agaccgcggc ggcgacgctg accaagccgc agtacatggt caacgtcgtg    2040
cgtacgtcgc tgcaggcgct gtcggccgtg ctcggcggcg cgcagtcgct gcacaccaac    2100
ggctacgacg aagccttcgc gatcccgacc gaggatgcga tgaagatggc gctgcgcacg    2160
cagcagatca ttgccgagga gagtggtgtc gccgacgtga tcgacccgct gggtggcagc    2220
tactacgtcg aggcgctgac caccgagtac gagaagaaga tcttcgagat cctcgaggaa    2280
gtcgagaagc gcgtggcac catcaagctg atcgagcagg gctggttcca gaagcagatt    2340
gcggacttcg cttacgagac cgcgctgcgc aagcagtccg gccagaagcc ggtgatcggg    2400
gtgaaccgct tcgtcgagaa cgaagaggac gtcaagatcg agatccaccc gtacgacaac    2460
acgacggccg aacgccagat tcccgcacg cgccgcgttc gcgccgagcg cgacgaggcc    2520
aaggtgcaag cgatgctcga ccaactggtg gctgtcgcca aggacgagtc ccagaacctg    2580
atgccgctga ccatcgaact ggtgaaggcc ggcgcaacga tggggacat cgtcgagaag    2640 ctgaagggga tctggggtac ctaccgcgag acgccggtct tctga                   2685
```

<210> SEQ ID NO 6
<211> LENGTH: 10663
<212> TYPE: DNA
<213> ORGANISM: Artificial Sequence
<220> FEATURE:
<223> OTHER INFORMATION: Description of Artificial Sequence: Synthetic
      vector polynucleotide

<400> SEQUENCE: 6

```
accttcggga gcgcctgaag cccgttctgg acgccctggg gccgttgaat cgggatatgc      60
aggccaaggc cgccgcgatc atcaaggccg tgggcgaaaa gctgctgacg aacagcggg     120 aagtccagcg ccagaaacag gcccagcgcc agcaggaacg cgggcgcgca catttccccg    180
aaaagtgcca cctgggatga atgtcagcta ctgggctatc tggacaaggg aaaacgcaag    240
cgcaaagaga aagcaggtag cttgcagtgg gcttacatgg cgatagctag actgggcggt    300
tttatggaca gcaagcgaac cggaattgcc agctggggcg ccctctggta aggttgggaa    360
gccctgcaaa gtaaactgga tggctttctt gccgccaagg atctgatggc gcaggggatc    420
aagatctgat caagagacag gatgaggatc gtttcgcatg attgaacaag atggattgca    480
cgcaggttct ccggccgctt gggtggagag ctattcggc tatgactggg cacaacagac    540
aatcggctgc tctgatgccg ccgtgttccg gctgtcagcg caggggcgcc cggttctttt    600
tgtcaagacc gacctgtccg gtgccctgaa tgaactgcag gacgaggcag cgcggctatc    660
gtggctggcc acgacgggcg ttccttgcgc agctgtgctc gacgttgtca ctgaagcggg    720
aagggactgg ctgctattgg gcgaagtgcc ggggcaggat ctcctgtcat ctcaccttgc    780
tcctgccgag aaagtatcca tcatggctga tgcaatgcgg cggctgcata cgcttgatcc    840
ggctacctgc ccattcgacc accaagcgaa acatcgcatc gagcgagcac gtactcggat    900
ggaagccggt cttgtcgatc aggatgatct ggacgaagag catcagggc tcgcgccagc    960 cgaactgttc gccaggctca aggcgcgcat gcccgacggc gaggatctcg tcgtgaccca   1020
tggcgatgcc tgcttgccga atatcatggt ggaaaatggc cgcttttctg gattcatcga   1080
ctgtggccgg ctgggtgtgg cggaccgcta tcaggacata gcgttggcta cccgtgatat   1140
tgctgaagag cttggcggcg aatgggctga ccgcttcctc gtgctttacg gtatcgccgc   1200
tcccgattcg cagcgcatcg ccttctatcg ccttcttgac gagttcttct gagcgggact   1260
ctggggttcg aaatgaccga ccaagcgacg cccaacctgc catcacgaga tttcgattcc   1320
```

```
accgccgcct tctatgaaag gttgggcttc ggaatcgttt tccggacgcg cggctggatg   1380
atcctccagc gcgggatct catgctggag ttcttcgccc accccatgg gcaaatatta    1440
tacgcaaggc gacaaggtgc tgatgccgct ggcgattcag gttcatcatg ccgtttgtga   1500
tggcttccat gtcggcagaa tgcttaatga attacaacag tttttatgca tgcgcccaat   1560
acgcaaaccg cctctccccg cgcgttggcc gattcattaa tgcagctggc acgacaggtt   1620
tcccgactgg aaagcgggca gtgagcgcaa cgcaattaat gtgagttagc tcactcatta   1680
ggcaccccag gctttacact ttatgcttcc ggctcgtatg ttgtgtggaa ttgtgagcgg   1740
ataacaattt cacacaggaa acagctatga ccatgattac gccaagcgcg caattaaccc   1800
tcactaaagg gaacaaaagc tgggtaccgg gccccccctc gaggtcgacg gtatcgataa   1860
gcttgatatc gcagaattc gcccttcagc gacttgcaac cttcttcacc ggaaacaata   1920
gctcgccatg gaccaaaccc caattcgcgt tcttctcgcc aaagtcggcc tcgacggcca   1980
tgaccgaggc gtcaaggtcg tcgctcgcgc gctgcgcgac gccggcatgg acgtcatcta   2040
ctccggcctt catcgcacgc ccgaagaggt ggtcaacacc gccatccagg aagacgtgga   2100
cgtgctgggt gtaagcctcc tgtccggcgt gcagctcacg gtcttcccca agatcttcaa   2160
gctcctggac gagagaggcg ctggcgactt gatcgtgatc gccggtggcg tgatgccgga   2220
cgaggacgcc gcgccatcc gcaagctcgg cgtgcgcgag gtgctcctgc aggacacgcc   2280
cccgcaggcc atcatcgact cgatccgctc cttggtcgcc gcgcgcggcg cccgctgaca   2340
ttggaggcac gccatggaag agtggaactt tccggtcgag tatgacgaga actacttgcc   2400
gccggccgac agccggtatt ggtttccgcg acgcgaaacg atgccggcgg cggagcgtga   2460
caaggccatc ctcggtcgcc tgcagcaggt atgtcagtac gcctgggagc acgcaccgtt   2520
ctatcgccgc aaatgggagg aggccggctt ccaacccagt cagctgaagt cgttggagga   2580
cttcgaggct cgcgtaccgg tggtgaagaa gacagacctg cgtgaatcgc aggccgcgca   2640
cccgccgttc ggcgactacg tgtgcgtgcc gaattccgaa atctttcacg tccacggaac   2700
cagcggcacc accgggcgcc cgaccgcttt cggcatcgt cgggccgact ggcgcgccat   2760
cgccaacgcg cacgcccgga tcatgtgggg catgggcatc cgcccgggcg acctggtctg   2820
cgtcgcagcc gttttcagcc tctatatggg tagctggggt gcgctggccg gcgcggagcg   2880
gttgcgcgcc aaggcctttc ccttcggcgc cggcgcgccc ggcatgagtg cccgcctggt   2940
gcaatggctc gacaccatga agccggcggc cttctacggc acgccaagct acgcgatcca   3000
tctcgctgag gtagcgcgcg aggagaagct gaatccgcgc aacttcggtc tgaagtgcct   3060
gttcttcagc ggcgagccgg gcgcttcggt gcctggcgtc aaggaccgta tcgaggaggc   3120
ttatggcgcc aaggtctacg actgcggttc gatggccgag atgtcccctt tcatgaacgt   3180
cgccggcacc gaacagagca acgacggcat gctgtgctgg caggacatca tctacaccga   3240
ggtctgtgac ccgccaaata tgcggcgcgt gccctacggc cagcgcggca cgccggtgta   3300
cacccacttg gagcgcacca gccagccgat gatccggctg ctctcgggcg acctcacgct   3360
gtggacgaac gacgagaatc cctgcggccg cacctatccc cggctgccgc aaggaatctt   3420
tggccgcatc gacgacatgt tcaccatccg cggcgagaac atttacccga gcgagatcga   3480
cgcagcactg aaccagatgt cgggctacgg cggtgagcac cggatcgtca tcacgcgcga   3540
gtcggcgatg gacgagctct tgctgcgcgt cgaacccagc gagagcgttc acgcggcggg   3600
ggctgctgca ctggagacgt tccgcacaga agcatcgcac cgggttcaga ccgtgctcgg   3660
```

-continued

```
cgtccgtgcc aaggtggaac tggtcgcgcc gaactcgatc gcgcgcaccg acttcaaggc    3720
gcggcgcgtg atcgacgacc gcgaagtgtt ccgggcgctg aaccagcaac tgcaatcgag    3780
cgcctgagca ggcagggacc ggaatgactt acgttccctc atccgccttg ctcgagcaac    3840
tccgagccgg caatacctgg gcgcttggcc gcctgatctc gcgcgccgag gccggtgtgg    3900
ccgaggcgcg gccagcattg gccgaggtct atcggcacgc cggctcggcg catgtgatcg    3960
gtctcaccgg ggtgccgggg agtggcaagt cgactctcgt ggcgaagctc acggccgccc    4020
tgcgcaagcg tggtgaaaag gtcggcatcg tcgcaatcga tccgtcgagc ccgtactcgg    4080
gcggtgcgat cctcggcgac cgtatccgaa tgaccgaact cgccaacgat ccggcgtat    4140
tcatccgcag catggccacg cgcggcgcga cgggggggcat ggcgcgtgcc gccctcgacg    4200
ccgtggacct gctggatgtc gccggctatc acaccatcat cctggagact gtcggagtcg    4260
gtcaggacga ggtggaggtg gcgcacgcat cggacacgac agtcgtcgta tcggcgccag    4320
gccttggaga cgagatccag gccatcaaag ccggcgtcct ggaaatcgcc gacatccatg    4380
ttgtcagcaa gtgtgaccgc gacgacgcga atcgcacgct caccgatctc aagcagatgc    4440
tgacgctcgg caccatggtc gggcccaagc gcgcatgggc gatcccggtc gtcggtgtca    4500
gttcgtacac aggcgaaggc gtcgacgacc tgctcggtcg catcgccgcc caccgccagg    4560
cgacggccga caccgaactc ggccgcgaac ggcgccgtcg cgtagccgaa ttccgccttc    4620
agaagaccgc cgagacgctg ctcctggagc gattcaccac cggagcgcag cccttctcgc    4680
ctgcgctcgc agacagcctc agcaaccgtg cgtcggatcc ctacgccgca gcacgcgaac    4740
tcatcgcccg aacgatccgc aaggagtact cgaatgacct ggcttgagcc gcagataaag    4800
tcccaactcc aatcggagcg caaggactgg gaagcgaacg aagtcggcgc cttcttgaag    4860
aaggcgcccg agcgcaagga gcagttccac acgatcgggg acttcccggt ccagcgcacc    4920
tacaccgctg ccgacatcgc cgacacgccg ctggaggaca tcggtcttcc ggggcgctac    4980
ccgttcacgc gcgggcccta cccgacgatg taccgcagcc gcacctggac gatgcgccag    5040
atcgccggct tcggcaccgg cgaggacacc aacaagcgct tcaagtatct gatcgcgcag    5100
ggccagaccg gcatctccac cgacttcgac atgcccacgc tgatgggcta cgactccgac    5160
caccccgatga gcgacggcga ggtcggccgc gagggcgtgg cgatcgacac gctggccgac    5220
atggaggcgc tgctgccgga catcgacctc gagaagatct cggtctcgtt cacgatcaac    5280
ccgagcgcct ggatcctgct cgcgatgtac gtggcgctcg gcgagaagcg cggctacgac    5340
ctgaacaagc tgtcgggcac ggtgcaggcc gacatcctga aggagtacat ggcgcagaag    5400
gagtacatct acccgatcgc gccgtcggtg cgcatcgtgc gcgacatcat cacctacagc    5460
gcgaagaacc tgaagcgcta caacccgatc aacatctcgg gctaccacat cagcgaggcc    5520
ggctcctcgc cgctccagga ggcggccttc acgctggcca acctgatcac ctacgtgaac    5580
gaggtgacga agaccggtat gcacgtcgac gaattcgcgc gcggttggc cttcttcttc    5640
gtgtcgcaag gtgacttctt cgaggaggtc gcgaagttcc gcgccctgcg ccgctgctac    5700
gcgaagatca tgaaggagcg cttcggtgca agaaatccgg aatcgatgcg gttgcgcttc    5760
cactgtcaga ccgcggcggc gacgctgacc aagccgcagt acatggtcaa cgtcgtgcgt    5820
acgtcgctgc aggcgctgtc ggccgtgctc ggcggcgcgc agtcgctgca caccaacggc    5880
tacgacgaag ccttcgcgat cccgaccgag gatgcgatga agatggcgct gcgcacgcag    5940
cagatcattg ccgaggagag tggtgtcgcc gacgtgatcg acccgctggg tggcagctac    6000
tacgtcgagg cgctgaccac cgagtacgag aagaagatct tcgagatcct cgaggaagtc    6060
```

```
gagaagcgcg gtggcaccat caagctgatc gagcagggct ggttccagaa gcagattgcg    6120
gacttcgctt acgagaccgc gctgcgcaag cagtccggcc agaagccggt gatcggggtg    6180
aaccgcttcg tcgagaacga agaggacgtc aagatcgaga tccacccgta cgacaacacg    6240
acggccgaac gccagatttc ccgcacgcgc cgcgttcgcg ccgagcgcga cgaggccaag    6300
gtgcaagcga tgctcgacca actggtggct gtcgccaagg acgagtccca gaacctgatg    6360
ccgctgacca tcgaactggt gaaggccggc gcaacgatgg gggacatcgt cgagaagctg    6420
aaggggatct ggggtaccta ccgcgagacg ccggtcttct gagcgtcggc cggccatgtc    6480
gggatccagc atgctgtctc gtgccgaggt gcgccaactg aagtcggcgg tgcgccgcga    6540
ggcgaacccg gctgcggccg agcggctgct ggccgacagc gtgcgaaagg acacgacaa    6600
gctggcgctg catcgatact tggcactgca cagaattgac gcggcgcggt gcgcccccta    6660
cgaggattac tgctgtcagg tggccggccg tttgccaggc gagtcgctgc gtcgggtcct    6720
ccgtcacgca ggctggatcg gctgagacgc tgagcacggc gcaaggagtg gtggcatgaa    6780
cagcgatggc atatcacacg accccgtcg tggcgacgac ggtacgacgt cattggccgg    6840
cggtacacgg gtcgagaaga acagcccgta catgcaggcg atcggcgtcg tagatgaatt    6900
gaacagcctg atcggcatgg caatcgcttc ggagtgcggc tccgatctcc gcgtggtgct    6960
gtcggaaacg caggacgaac tggtggcgct gtccaccgag ctctcgtcgc cgggcagcat    7020
cgtcttgacg cttgcggcgc tgcagcgtgt cgacaaggag ctgaccaggt ggcttgcgga    7080
cttgcctccg gcggccggca tcgtcctgcc gcgcggaacg atggccgcgg cgctgtgctt    7140
caaggcacga gcgacatgtc gcacgctaga gcgcgaactc gtcggtctcg aggaggcgga    7200
tcgcgagtct tgcgcggatt cgttgcgcct gccgtatgtc aaccggctgt ccgatcttct    7260
gcatgcgctc gcccgaactg tgaatcgacg tgccgacgcc gaggcgatcg tcagggccgc    7320
cggtgtccag gctggatcgg caagtcgag cgactgatac ttcgacctcg aaaggagcgg    7380
cgaagggcga attccagcac actggcggcc gttactagtt ctagagcggc cgccaccgcg    7440
gtggagctcc aattcgccct atagtgagtc gtattacgcg cgctcactgg ccgtcgtttt    7500
acaacgtcgt gactgggaaa accctggcgt tacccaactt aatcgccttg cagcacatcc    7560
cccttcgcc agctggcgta atagcgaaga ggcccgcacc gatcgccctt cccaacagtt    7620
gcgcagcctg aatggcgaat ggaaattgta agcgttaata ttttgttaaa attcgcgtta    7680
aattttgtt aaatcagctc attttttaac caataggccg actgcgatga gtggcagggc    7740
ggggcgtaat ttttttaagg cagttattgg tgcccttaaa cgcctggtgc tacgcctgaa    7800
taagtgataa taagcggatg aatggcagaa attcgaaagc aaattcgacc cggtcgtcgg    7860
ttcagggcag ggtcgttaaa tagccgctta tgtctattgc tggtttaccg gtttattgac    7920
taccggaagc agtgtgaccg tgtgcttctc aaatgcctga ggccagtttg ctcaggctct    7980
ccccgtggag gtaataattg acgatatgat catttattct gcctcccaga gcctgataaa    8040
aacggtgaat ccgttagcga ggtgccgccg gcttccattc aggtcgaggt ggcccggctc    8100
catgcaccgc gacgcaacgc ggggaggcag acaaggtata gggcggcgag gcggctacag    8160
ccgatagtct ggaacagcgc acttacgggt tgctgcgcaa cccaagtgct accggcgcgg    8220
cagcgtgacc cgtgtcggcg gctccaacgg ctcgccatcg tccagaaaac acggctcatc    8280
gggcatcggc aggcgctgct gcccgcgccg ttcccattcc tccgtttcgg tcaaggctgg    8340
caggtctggt tccatgcccg gaatgccggg ctggctgggg ggctcctcgc cggggccggt    8400
```

```
cggtagttgc tgctcgcccg gatacagggt cgggatgcgg cgcaggtcgc catgccccaa      8460
cagcgattcg tcctggtcgt cgtgatcaac caccacggcg gcactgaaca ccgacaggcg      8520
caactggtcg cggggctggc cccacgccac gcggtcattg accacgtagg ccgacacggt      8580
gccggggccg ttgagcttca cgacggagat ccagcgctcg gccaccaagt ccttgactgc      8640
gtattggacc gtccgcaaag aacgtccgat gagcttggaa agtgtcttct ggctgaccac      8700
cacggcgttc tggtggccca tctgcgccac gaggtgatgc agcagcattg ccgccgtggg      8760
tttcctcgca ataagcccgg cccacgcctc atgcgctttg cgttccgttt gcacccagtg      8820
accgggcttg ttcttggctt gaatgccgat ttctctggac tgcgtggcca tgcttatctc      8880
catgcggtag ggtgccgcac ggttgcggca ccatgcgcaa tcagctgcaa ctttccggca      8940
gcgcgacaac aattatgcgt tgcgtaaaag tggcagtcaa ttacagattt tctttaacct      9000
acgcaatgag ctattgcggg gggtgccgca atgagctgtt gcgtacccc cttttttaag      9060 ttgttgattt ttaagtcttt cgcatttcgc cctatatcta gttctttggt gcccaaagaa      9120
gggcacccct gcggggttcc cccacgcctt cggcgcggct ccccctccgg caaaaagtgg      9180
cccctccggg gcttgttgat cgactgcgcg gccttcggcc ttgcccaagg tggcgctgcc      9240
cccttggaac ccccgcactc gccgccgtga ggctcggggg gcaggcgggc gggcttcgcc      9300
ttcgactgcc cccactcgca taggcttggg tcgttccagg cgcgtcaagg ccaagccgct      9360
gcgcggtcgc tgcgcgagcc ttgacccgcc ttccacttgg tgtccaaccg gcaagcgaag      9420
cgcgcaggcc gcaggccgga ggcttttccc cagagaaaat taaaaaaatt gatggggcaa      9480
ggccgcaggc cgcgcagttg gagccggtgg gtatgtggtc gaaggctggg tagccggtgg      9540
gcaatccctg tggtcaagct cgtgggcagg cgcagcctgt ccatcagctt gtccagcagg      9600
gttgtccacg ggccgagcga agcgagccag ccggtggccg ctcgcggcca tcgtccacat      9660
atccacgggc tggcaaggga gcgcagcgac cgcgcagggc gaagcccgga gagcaagccc      9720
gtagggcgcc gcagccgccg taggcggtca cgactttgcg aagcaaagtc tagtgagtat      9780
actcaagcat tgagtggccc gccggaggca ccgccttgcg ctgccccgt cgagccggtt      9840 ggacaccaaa agggagggc aggcatggcg gcatacgcga tcatgcgatg caagaagctg      9900
gcgaaaatgg caacgtggc ggccagtctc aagcacgcct accgcgagcg cgagacgccc      9960
aacgctgacg ccagcaggac gccagagaac gagcactggg cggccagcag caccgatgaa     10020
gcgatgggcc gactgcgcga gttgctgcca gagaagcggc gcaaggacgc tgtgttggcg     10080
gtcgagtacg tcatgacggc cagcccggaa tggtggaagt cggccagcca agaacagcag     10140
gcggcgttct tcgagaaggc gcacaagtgg ctggcggaca agtacggggc ggatcgcatc     10200
gtgacggcca gcatccaccg tgacgaaacc agcccgcaca tgaccgcgtt cgtggtgccg     10260
ctgacgcagg acggcaggct gtcggccaag gagttcatcg gcaacaaagc gcagatgacc     10320
cgcgaccaga ccacgtttgc ggccgctgtg gccgatctag gctgcaacg gggcatcgag     10380 ggcagcaagg cacgtcacac gcgcattcag gcgttctacg aggccctgga gcggccacca     10440
gtgggccacg tcaccatcag cccgcaagcg gtcgagccac gcgcctatgc accgcaggga     10500
ttggccgaaa agctgggaat ctcaaagcgc gttgagacgc cggaagccgt ggccgaccgg     10560
ctgacaaaag cggttcggca ggggtatgag cctgccctac aggccgccgc aggagcgcgt     10620
gagatgcgca agaaggccga tcaagcccaa gagacggccc gag                       10663

<210> SEQ ID NO 7
<211> LENGTH: 8235
```

<212> TYPE: DNA
<213> ORGANISM: Artificial Sequence
<220> FEATURE:
<223> OTHER INFORMATION: Description of Artificial Sequence: Synthetic vector polynucleotide

<400> SEQUENCE: 7

| | | | | | |
|---|---|---|---|---|---|
| accttcggga | gcgcctgaag | cccgttctgg | acgccctggg | gccgttgaat | cgggatatgc | 60 |
| aggccaaggc | cgccgcgatc | atcaaggccg | tgggcgaaaa | gctgctgacg | aacagcggg | 120 |
| aagtccagcg | ccagaaacag | gcccagcgcc | agcaggaacg | cgggcgcgca | catttccccg | 180 |
| aaaagtgcca | cctgggatga | atgtcagcta | ctgggctatc | tggacaaggg | aaaacgcaag | 240 |
| cgcaaagaga | aagcaggtag | cttgcagtgg | gcttacatgg | cgatagctag | actgggcggt | 300 |
| tttatggaca | gcaagcgaac | cggaattgcc | agctggggcg | ccctctggta | aggttgggaa | 360 |
| gccctgcaaa | gtaaactgga | tggctttctt | gccgccaagg | atctgatggc | gcagggggatc | 420 |
| aagatctgat | caagagacag | gatgaggatc | gtttcgcatg | attgaacaag | atggattgca | 480 |
| cgcaggttct | ccggccgctt | gggtggagag | gctattcggc | tatgactggg | cacaacagac | 540 |
| aatcggctgc | tctgatgccg | ccgtgttccg | gctgtcagcg | caggggcgcc | cggttctttt | 600 |
| tgtcaagacc | gacctgtccg | gtgccctgaa | tgaactgcag | gacgaggcag | cgcggctatc | 660 |
| gtggctggcc | acgacgggcg | ttccttgcgc | agctgtgctc | gacgttgtca | ctgaagcggg | 720 |
| aagggactgg | ctgctattgg | gcgaagtgcc | ggggcaggat | ctcctgtcat | ctcaccttgc | 780 |
| tcctgccgag | aaagtatcca | tcatggctga | tgcaatgcgg | cggctgcata | cgcttgatcc | 840 |
| ggctacctgc | ccattcgacc | accaagcgaa | acatcgcatc | gagcgagcac | gtactcggat | 900 |
| ggaagccggt | cttgtcgatc | aggatgatct | ggacgaagag | catcaggggc | tcgcgccagc | 960 |
| cgaactgttc | gccaggctca | aggcgcgcat | gcccgacggc | gaggatctcg | tcgtgaccca | 1020 |
| tggcgatgcc | tgcttgccga | atatcatggt | ggaaaatggc | cgcttttctg | gattcatcga | 1080 |
| ctgtggccgg | ctgggtgtgg | cggaccgcta | tcaggacata | gcgttggcta | cccgtgatat | 1140 |
| tgctgaagag | cttggcggcg | aatgggctga | ccgcttcctc | gtgctttacg | gtatcgccgc | 1200 |
| tcccgattcg | cagcgcatcg | ccttctatcg | ccttcttgac | gagttcttct | gagcgggact | 1260 |
| ctggggttcg | aaatgaccga | ccaagcgacg | cccaacctgc | catcacgaga | tttcgattcc | 1320 |
| accgccgcct | tctatgaaag | gttgggcttc | ggaatcgttt | tccggacgc | cggctggatg | 1380 |
| atcctccagc | gcggggatct | catgctggag | ttcttcgccc | accccatgg | gcaaatatta | 1440 |
| tacgcaaggc | gacaaggtgc | tgatgccgct | ggcgattcag | gttcatcatg | ccgtttgtga | 1500 |
| tggcttccat | gtcggcagaa | tgcttaatga | attacaacag | ttttatgca | tgcgcccaat | 1560 |
| acgcaaaccg | cctctccccg | cgcgttggcc | gattcattaa | tgcagctggc | acgacaggtt | 1620 |
| tcccgactgg | aaagcgggca | gtgagcgcaa | cgcaattaat | gtgagttagc | tcactcatta | 1680 |
| ggcaccccag | gctttacact | ttatgcttcc | ggctcgtatg | ttgtgtggaa | ttgtgagcgg | 1740 |
| ataacaattt | cacacaggaa | acagctatga | ccatgattac | gccaagcgcg | caattaaccc | 1800 |
| tcactaaagg | gaacaaaagc | tgggtaccgg | gccccccctc | gaggtcgacg | gtatcgataa | 1860 |
| gcttgataaa | tttagatctg | gagaccggaa | tgacttacgt | tccctcatcc | gccttgctcg | 1920 |
| agcaactccg | agccggcaat | acctgggcgc | ttggccgcct | gatctcgcgc | gccgaggccg | 1980 |
| gtgtggccga | ggcgcggcca | gcattggccg | aggtctatcg | gcacgccggc | tcggcgcatg | 2040 |
| tgatcggtct | caccggggtg | ccggggagtg | gcaagtcgac | tctcgtggcg | aagctcacgg | 2100 |
| ccgccctgcg | caagcgtggt | gaaaaggtcg | gcatcgtcgc | aatcgatccg | tcgagcccgt | 2160 |

```
actcgggcgg tgcgatcctc ggcgaccgta tccgaatgac cgaactcgcc aacgattccg    2220
gcgtattcat ccgcagcatg ccacgcgcg gcgcgacggg gggcatggcg cgtgccgccc    2280
tcgacgccgt ggacctgctg gatgtcgccg gctatcacac catcatcctg gagactgtcg    2340
gagtcggtca ggacgaggtg gaggtggcgc acgcatcgga cacgcagatc gtcgtatcgg    2400
cgccaggcct tggagacgag atccaggcca tcaaagccgg cgtcctggaa atcgccgaca    2460
tccatgttgt cagcaagtgt gaccgcgacg acgcgaatcg cacgctcacc gatctcaagc    2520
agatgctgac gctcggcacc atggtcgggc ccaagcgcgc atgggcgatc ccggtcgtcg    2580
gtgtcagttc gtacacaggc gaaggcgtcg acgacctgct cggtcgcatc gccgcccacc    2640
gccaggcgac ggccgacacc gaactcggcc gcgaacggcg ccgtcgcgta gccgaattcc    2700
gccttcagaa gaccgccgag acgctgctcc tggagcgatt caccaccgga gcgcagccct    2760
tctcgcctgc gctcgcagac agcctcagca accgtgcgtc ggatccctac gccgcagcac    2820
gcgaactcat cgcccgaacg atcgcaagg agtactcgaa tgacctggct tgcgccaagc    2880
ttaccataac ctggcttgag ccgcagataa agtcccaact ccaatcggag cgcaaggact    2940
gggaagcgaa cgaagtcggc gccttcttga agaaggcgcc cgagcgcaag gagcagttcc    3000
acacgatcgg ggacttcccg gtccagcgca cctacaccgc tgccgacatc gccgacacgc    3060
cgctggagga catcggtctt ccggggcgct acccgttcac gcgcgggccc tacccgacga    3120
tgtaccgcag ccgcacctgg acgatgcgcc agatcgccgg cttcggcacc ggcgaggaca    3180
ccaacaagcg cttcaagtat ctgatcgcgc agggccagac cggcatctcc accgacttcg    3240
acatgcccac gctgatgggc tacgactccg accacccgat gagcgacggc gaggtcggcc    3300
gcgagggcgt ggcgatcgac acgctggccg acatggaggc gctgctgccg acatcgaccc    3360
tcgagaagat ctcggtctcg ttcacgatca acccgagcgc ctggatcctg ctcgcgatgt    3420
acgtggcgct cggcgagaag cgcggctacg acctgaacaa gctgtcgggc acggtgcagg    3480
ccgacatcct gaaggagtac atggcgcaga aggagtacat ctacccgatc gcgccgtcgg    3540
tgcgcatcgt gcgcgacatc atcacctaca gcgcgaagaa cctgaagcgc tacaacccga    3600
tcaacatctc gggctaccac atcagcgagg ccggctcctc gccgctccag gaggcggcct    3660
tcacgctggc caacctgatc acctacgtga acgaggtgac gaagaccggt atgcacgtcg    3720
acgaattcgc ccgcggttg gccttcttct cgtgtcgca aggtgacttc ttcgaggagg    3780
tcgcgaagtt ccgcgccctg cgccgctgct acgcgaagat catgaaggag cgcttcggtg    3840
caagaaatcc ggaatcgatg cggttgcgct tccactgtca gaccgcggcg gcgacgctga    3900
ccaagccgca gtacatggtc aacgtcgtgc gtacgtcgct gcaggcgctg tcggccgtgc    3960
tcggcggcgc gcagtcgctg cacaccaacg gctacgacga agccttcgcg atcccgaccg    4020
aggatgcgat gaagatggcg ctgcgcacgc agcagatcat tgccgaggag agtggtgtcg    4080
ccgacgtgat cgacccgctg ggtggcagct actacgtcga ggcgctgacc accgagtacg    4140
agaagaagat cttcgagatc ctcgaggaag tcgagaagcg cggtggcacc atcaagctga    4200
tcgagcaggg ctggttccag aagcagattg cggacttcgc ttacgagacc gcgctgcgca    4260
agcagtccgg ccagaagccg gtgatcgggg tgaaccgctt cgtcgagaac gaagaggacg    4320
tcaagatcga gatccacccg tacgacaaca cgacggccga acgccagatt tcccgcacgc    4380
gccgcgttcg cgccgagcgc gacgaggcca aggtgcaagc gatgctcgac caactggtgg    4440
ctgtcgccaa ggacgagtcc cagaacctga tgccgctgac catcgaactg gtgaaggccg    4500
```

```
gcgcaacgat gggggacatc gtcgagaagc tgaagggggat ctggggtacc taccgcgaga    4560
cgccggtctt ctgagcacta gttggagagc ttcccaccat ggaccaaacc ccaattcgcg    4620
ttcttctcgc caaagtcggc ctcgacggcc atgaccgagg cgtcaaggtc gtcgctcgcg    4680
cgctgcgcga cgccggcatg gacgtcatct actccggcct tcatcgcacg cccgaagagg    4740
tggtcaacac cgccatccag gaagacgtgg acgtgctggg tgtaagcctc ctgtccggcg    4800
tgcagctcac ggtcttcccc aagatcttca agctcctgga cgagagaggc gctggcgact    4860
tgatcgtgat cgccggtggc gtgatgccgg acgaggacgc cgcggccatc cgcaagctcg    4920
gcgtgcgcga ggtgctcctg caggacacgc ccccgcaggc catcatcgac tcgatccgct    4980
ccttggtcgc cgcgcgcggc gcccgctgaa agggcgagct ccaattcgcc ctatagtgag    5040
tcgtattacg cgcgctcact ggccgtcgtt ttacaacgtc gtgactggga aaaccctggc    5100
gttacccaac ttaatcgcct tgcagcacat ccccctttcg ccagctggcg taatagcgaa    5160
gaggcccgca ccgatcgccc ttcccaacag ttgcgcagcc tgaatggcga atggaaattg    5220
taagcgttaa tattttgtta aaattcgcgt taaattttg ttaaatcagc tcatttttta    5280
accaataggc cgactgcgat gagtggcagg gcggggcgta attttttta ggcagttatt    5340
ggtgcccttta aacgcctggt gctacgcctg aataagtgat aataagcgga tgaatggcag    5400
aaattcgaaa gcaaattcga cccggtcgtc ggttcagggc agggtcgtta aatagccgct    5460
tatgtctatt gctggtttac cggtttattg actaccggaa gcagtgtgac cgtgtgcttc    5520
tcaaatgcct gaggccagtt tgctcaggct ctcccgtgg aggtaataat tgacgatatg    5580
atcatttatt ctgcctccca gagcctgata aaaacggtga atccgttagc gaggtgccgc    5640
cggcttccat tcaggtcgag gtggcccggc tccatgcacc gcgacgcaac gcggggaggc    5700
agacaaggta tagggcggcg aggcggctac agccgatagt ctggaacagc gcacttacgg    5760
gttgctgcgc aacccaagtg ctaccggcgc ggcagcgtga cccgtgtcgg cggctccaac    5820
ggctcgccat cgtccagaaa acacggctca tcgggcatcg gcaggcgctg ctcccgcgc    5880
cgttcccatt cctccgtttc ggtcaaggct ggcaggtctg gttccatgcc cggaatgccg    5940
ggctggctgg gcggctcctc gccggggccg gtcggtagtt gctgctcgcc cggatacagg    6000
gtcgggatgc ggcgcaggtc gccatgcccc aacagcgatt cgtcctggtc gtcgtgatca    6060
accaccacgg cggcactgaa caccgacagg cgcaactggt cgcggggctg gccccacgcc    6120
acgcggtcat tgaccacgta ggccgacacg gtgccggggc cgttgagctt cacgacggag    6180
atccagcgct cggccaccaa gtccttgact gcgtattgga ccgtccgcaa agaacgtccg    6240
atgagcttgg aaagtgtctt ctggctgacc accacggcgt tctggtggcc catctgcgcc    6300
acgaggtgat gcagcagcat tgccgccgtg ggtttcctcg caataagccc ggcccacgcc    6360
tcatgcgctt tgcgttccgt ttgcacccag tgaccgggct tgttcttggc ttgaatgccg    6420
atttctctgg actgcgtggc catgcttatc tccatgcggt agggtgccgc acggttgcgg    6480
caccatgcgc aatcagctgc aacttttcgg cagcgcgaca acaattatgc gttgcgtaaa    6540
agtggcagtc aattacagat tttctttaac ctacgcaatg agctattgcg gggggtgccg    6600
caatgagctg ttgcgtaccc cccttttttta agttgttgat ttttaagtct ttcgcatttc    6660
gccctatatc tagttctttg gtgcccaaag aagggcaccc ctgcggggtt ccccacgcc    6720
ttcggcgcgg ctccccctcc ggcaaaaagt ggcccctccg ggcttgttg atcgactgcg    6780
cggccttcgg ccttgcccaa ggtggcgctg ccccccttgga accccgcac tcgccgccgt    6840
gaggctcggg gggcaggcgg gcgggcttcg ccttcgactg ccccccactcg cataggcttg    6900
```

-continued

```
ggtcgttcca ggcgcgtcaa ggccaagccg ctgcgcggtc gctgcgcgag ccttgacccg    6960
ccttccactt ggtgtccaac cggcaagcga agcgcgcagg ccgcaggccg gaggcttttc    7020
cccagagaaa attaaaaaaa ttgatggggc aaggccgcag gccgcgcagt tggagccggt    7080
gggtatgtgg tcgaaggctg ggtagccggt gggcaatccc tgtggtcaag ctcgtgggca    7140
ggcgcagcct gtccatcagc ttgtccagca gggttgtcca cgggccgagc gaagcgagcc    7200
agccggtggc cgctcgcggc catcgtccac atatccacgg gctggcaagg gagcgcagcg    7260
accgcgcagg gcgaagcccg gagagcaagc ccgtagggcg ccgcagccgc cgtaggcggt    7320
cacgactttg cgaagcaaag tctagtgagt atactcaagc attgagtggc ccgccggagg    7380
caccgccttg cgctgccccc gtcgagccgg ttggacacca aaagggaggg gcaggcatgg    7440
cggcatacgc gatcatgcga tgcaagaagc tggcgaaaat gggcaacgtg gcggccagtc    7500
tcaagcacgc ctaccgcgag cgcgagacgc ccaacgctga cgccagcagg acgccagaga    7560
acgagcactg ggcggccagc agcaccgatg aagcgatggg ccgactgcgc gagttgctgc    7620
cagagaagcg gcgcaaggac gctgtgttgg cggtcgagta cgtcatgacg ccagcccgg    7680 aatggtggaa gtcggccagc caagaacagc aggcggcgtt cttcgagaag gcgcacaagt    7740
ggctggcgga caagtacggg gcggatcgca tcgtgacggc cagcatccac cgtgacgaaa    7800
ccagcccgca catgaccgcg ttcgtggtgc cgctgacgca ggacggcagg ctgtcggcca    7860
aggagttcat cggcaacaaa gcgcagatga cccgcgacca gaccacgttt gcggccgctg    7920
tggccgatct agggctgcaa cggggcatcg agggcagcaa ggcacgtcac acgcgcattc    7980
aggcgttcta cgaggccctg gagcggccac cagtgggcca cgtcaccatc agcccgcaag    8040
cggtcgagcc acgcgcctat gcaccgcagg gattggccga aaagctggga atctcaaagc    8100
gcgttgagac gccggaagcc gtggccgacc ggctgacaaa agcggttcgg caggggtatg    8160
agcctgccct acaggccgcc gcaggagcgc gtgagatgcg caagaaggcc gatcaagccc    8220
aagagacggc ccgag                                                    8235
```

```
<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cagcgacttg caaccttctt caccgg                                          26

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtatcagtcg ctccgacttg ccgatcc                                         27

<210> SEQ ID NO 10
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 10
ggaattgtga gcggataa                                                     18

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cagcgccccg ggatactcga ccggaaagtt cc                                     32

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gagtatcccg gggcgctgaa ccagcaactg                                        30

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atggcctgga tctcgtctc                                                    19

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atagcaatgc atgaccggaa tgacttacgt tccc                                   34

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
actttaagct tggcgcaagc caggtcattc g                                      31

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 16
aaaaagctta ccataacctg gcttgagccg                                       30

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ataccgacta gtgctcagaa gaccggcgtc tc                                    32

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aaatctacta gttggagatc ccaccatgga ccaaatcccg                            40

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
taggctgagc tccaagcttc gaattgagct cgccctttca g                          41

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaatttagat ctggagaccg gaatgactta cgttccc                               37

<210> SEQ ID NO 21
<211> LENGTH: 562
<212> TYPE: PRT
<213> ORGANISM: Aquincola tertiaricarbonis

<400> SEQUENCE: 21

Met Thr Trp Leu Glu Pro Gln Ile Lys Ser Gln Leu Gln Ser Glu Arg
1               5                   10                  15

Lys Asp Trp Glu Ala Asn Glu Val Gly Ala Phe Leu Lys Lys Ala Pro
            20                  25                  30

Glu Arg Lys Glu Gln Phe His Thr Ile Gly Asp Phe Pro Val Gln Arg
        35                  40                  45

Thr Tyr Thr Ala Ala Asp Ile Ala Asp Thr Pro Leu Glu Asp Ile Gly
    50                  55                  60

Leu Pro Gly Arg Tyr Pro Phe Thr Arg Gly Pro Tyr Pro Thr Met Tyr

```
            65                  70                  75                  80
        Arg Ser Arg Thr Trp Thr Met Arg Gln Ile Ala Gly Phe Gly Thr Gly
                            85                  90                  95
        Glu Asp Thr Asn Lys Arg Phe Lys Tyr Leu Ile Ala Gln Gly Gln Thr
                           100                 105                 110
        Gly Ile Ser Thr Asp Phe Asp Met Pro Thr Leu Met Gly Tyr Asp Ser
                           115                 120                 125
        Asp His Pro Met Ser Asp Gly Glu Val Gly Arg Glu Gly Val Ala Ile
        130                 135                 140
        Asp Thr Leu Ala Asp Met Glu Ala Leu Leu Ala Asp Ile Asp Leu Glu
        145                 150                 155                 160
        Lys Ile Ser Val Ser Phe Thr Ile Asn Pro Ser Ala Trp Ile Leu Leu
                           165                 170                 175
        Ala Met Tyr Val Ala Leu Gly Glu Lys Arg Gly Tyr Asp Leu Asn Lys
                           180                 185                 190
        Leu Ser Gly Thr Val Gln Ala Asp Ile Leu Lys Glu Tyr Met Ala Gln
                           195                 200                 205
        Lys Glu Tyr Ile Tyr Pro Ile Ala Pro Ser Val Arg Ile Val Arg Asp
                           210                 215                 220
        Ile Ile Thr Tyr Ser Ala Lys Asn Leu Lys Arg Tyr Asn Pro Ile Asn
        225                 230                 235                 240
        Ile Ser Gly Tyr His Ile Ser Glu Ala Gly Ser Ser Pro Leu Gln Glu
                           245                 250                 255
        Ala Ala Phe Thr Leu Ala Asn Leu Ile Thr Tyr Val Asn Glu Val Thr
                           260                 265                 270
        Lys Thr Gly Met His Val Asp Glu Phe Ala Pro Arg Leu Ala Phe Phe
                           275                 280                 285
        Phe Val Ser Gln Gly Asp Phe Phe Glu Glu Val Ala Lys Phe Arg Ala
                           290                 295                 300
        Leu Arg Arg Cys Tyr Ala Lys Ile Met Lys Glu Arg Phe Gly Ala Arg
        305                 310                 315                 320
        Asn Pro Glu Ser Met Arg Leu Arg Phe His Cys Gln Thr Ala Ala Ala
                           325                 330                 335
        Thr Leu Thr Lys Pro Gln Tyr Met Val Asn Val Val Arg Thr Ser Leu
                           340                 345                 350
        Gln Ala Leu Ser Ala Val Leu Gly Gly Ala Gln Ser Leu His Thr Asn
                           355                 360                 365
        Gly Tyr Asp Glu Ala Phe Ala Ile Pro Thr Glu Asp Ala Met Lys Met
                           370                 375                 380
        Ala Leu Arg Thr Gln Gln Ile Ile Ala Glu Glu Ser Gly Val Ala Asp
        385                 390                 395                 400
        Val Ile Asp Pro Leu Gly Gly Ser Tyr Tyr Val Glu Ala Leu Thr Thr
                           405                 410                 415
        Glu Tyr Glu Lys Lys Ile Phe Glu Ile Leu Glu Glu Val Glu Lys Arg
                           420                 425                 430
        Gly Gly Thr Ile Lys Leu Ile Glu Gln Gly Trp Phe Gln Lys Gln Ile
                           435                 440                 445
        Ala Asp Phe Ala Tyr Glu Thr Ala Leu Arg Lys Gln Ser Gly Gln Lys
                           450                 455                 460
        Pro Val Ile Gly Val Asn Arg Phe Val Glu Asn Glu Glu Asp Val Lys
        465                 470                 475                 480
        Ile Glu Ile His Pro Tyr Asp Asn Thr Thr Ala Glu Arg Gln Ile Ser
                           485                 490                 495
```

Arg Thr Arg Arg Val Arg Ala Glu Arg Asp Glu Ala Lys Val Gln Ala
            500                 505                 510

Met Leu Asp Gln Leu Val Ala Val Ala Lys Asp Glu Ser Gln Asn Leu
        515                 520                 525

Met Pro Leu Thr Ile Glu Leu Val Lys Ala Gly Ala Thr Met Gly Asp
    530                 535                 540

Ile Val Glu Lys Leu Lys Gly Ile Trp Gly Thr Tyr Arg Glu Thr Pro
545                 550                 555                 560

Val Phe

<210> SEQ ID NO 22
<211> LENGTH: 136
<212> TYPE: PRT
<213> ORGANISM: Aquincola tertiaricarbonis

<400> SEQUENCE: 22

Met Asp Gln Ile Pro Ile Arg Val Leu Leu Ala Lys Val Gly Leu Asp
1               5                   10                  15

Gly His Asp Arg Gly Val Lys Val Val Ala Arg Ala Leu Arg Asp Ala
            20                  25                  30

Gly Met Asp Val Ile Tyr Ser Gly Leu His Arg Thr Pro Glu Glu Val
        35                  40                  45

Val Asn Thr Ala Ile Gln Glu Asp Val Asp Val Leu Gly Val Ser Leu
    50                  55                  60

Leu Ser Gly Val Gln Leu Thr Val Phe Pro Lys Ile Phe Lys Leu Leu
65                  70                  75                  80

Asp Glu Arg Gly Ala Gly Asp Leu Ile Val Ile Ala Gly Gly Val Met
                85                  90                  95

Pro Asp Glu Asp Ala Ala Ala Ile Arg Lys Leu Gly Val Arg Glu Val
            100                 105                 110

Leu Leu Gln Asp Thr Pro Pro Gln Ala Ile Ile Asp Ser Ile Arg Ser
        115                 120                 125

Leu Val Ala Ala Arg Gly Ala Arg
    130                 135

<210> SEQ ID NO 23
<211> LENGTH: 327
<212> TYPE: PRT
<213> ORGANISM: Methylibium petroleiphilum

<400> SEQUENCE: 23

Met Thr Tyr Val Pro Ser Phe Ala Leu Leu Glu Gln Leu Arg Ala Gly
1               5                   10                  15

Asn Thr Trp Ala Leu Gly Arg Leu Ile Ser Arg Ala Glu Ala Gly Val
            20                  25                  30

Ala Glu Ala Arg Pro Ala Leu Ala Glu Val Tyr Arg His Ala Gly Ser
        35                  40                  45

Ala His Val Ile Gly Leu Thr Gly Val Pro Gly Ser Gly Lys Ser Thr
    50                  55                  60

Leu Val Ala Lys Leu Thr Ala Ala Leu Arg Lys Arg Gly Glu Lys Val
65                  70                  75                  80

Gly Ile Val Ala Ile Asp Pro Ser Ser Pro Tyr Ser Gly Gly Ala Ile
                85                  90                  95

Leu Gly Asp Arg Ile Arg Met Thr Glu Leu Ala Asn Ser Gly Val
            100                 105                 110

```
Phe Ile Arg Ser Met Ala Thr Arg Gly Ala Thr Gly Met Ala Arg
            115                 120                 125

Ala Ala Leu Asp Ala Val Asp Leu Leu Asp Val Ala Gly Tyr His Thr
130                 135                 140

Ile Ile Leu Glu Thr Val Gly Val Gly Gln Asp Glu Val Glu Val Ala
145                 150                 155                 160

His Ala Ser Asp Thr Thr Val Val Ser Ala Pro Gly Leu Gly Asp
                165                 170                 175

Glu Ile Gln Ala Ile Lys Ala Gly Val Leu Glu Ile Ala Asp Ile His
            180                 185                 190

Val Val Ser Lys Cys Asp Arg Asp Ala Asn Arg Thr Leu Thr Asp
        195                 200                 205

Leu Lys Gln Met Leu Thr Leu Gly Thr Met Val Gly Pro Lys Arg Ala
210                 215                 220

Trp Ala Ile Pro Val Val Gly Val Ser Ser Tyr Thr Gly Glu Gly Val
225                 230                 235                 240

Asp Asp Leu Leu Gly Arg Ile Ala Ala His Arg Gln Ala Thr Ala Asp
                245                 250                 255

Thr Glu Leu Gly Arg Glu Arg Arg Arg Val Ala Glu Phe Arg Leu
                260                 265                 270

Gln Lys Thr Ala Glu Thr Leu Leu Leu Glu Arg Phe Thr Thr Gly Ala
    275                 280                 285

Gln Pro Phe Ser Pro Ala Leu Ala Asp Ser Leu Ser Asn Arg Ala Ser
        290                 295                 300

Asp Pro Tyr Ala Ala Arg Glu Leu Ile Ala Arg Thr Ile Arg Lys
305                 310                 315                 320

Glu Tyr Ser Asn Asp Leu Ala
                325

<210> SEQ ID NO 24
<211> LENGTH: 332
<212> TYPE: PRT
<213> ORGANISM: Xanthobacter autotrophicus

<400> SEQUENCE: 24

Met Met Ala Ala Tyr Val Pro Ser Leu Asp Leu Val Pro Arg Ile Ala
1               5                   10                  15

Ala Gly Asn Val Gly Ala Ile Ala Arg Leu Ile Ser Arg Ser Glu Ser
                20                  25                  30

Gly Met Pro Glu Ala Arg Pro Ala Leu Ala Glu Ile Tyr Arg Arg Ala
            35                  40                  45

Gly Arg Ala His Ile Ile Gly Ile Thr Gly Val Pro Gly Ser Gly Lys
        50                  55                  60

Ser Thr Leu Val Ala Arg Phe Ala Gln Met Leu Arg Ala Arg Gly Ser
65                  70                  75                  80

Lys Val Gly Ile Val Ala Val Asp Pro Ser Ser Pro Phe Ser Gly Gly
                85                  90                  95

Ser Ile Leu Gly Asp Arg Val Arg Met Asn Glu Leu Gly Met Asp Pro
            100                 105                 110

Gly Val Tyr Ile Arg Ser Met Ala Thr Arg Gly Ala Thr Gly Met
        115                 120                 125

Ala Arg Ala Ala Leu Asp Ala Val Asp Val Leu Asp Val Gly Gly Phe
    130                 135                 140

Asp Thr Val Ile Ile Glu Thr Val Gly Val Gly Gln Asp Glu Val Glu
145                 150                 155                 160
```

-continued

```
Ile Ala Arg Ala Ser His Thr Thr Val Val Ser Ala Pro Gly Leu
                165                 170                 175

Gly Asp Glu Ile Gln Ala Ile Lys Ala Gly Ile Leu Glu Ile Ala Asp
            180                 185                 190

Ile His Val Val Ser Lys Cys Asp Arg Ser Asp Ala Asn Arg Thr Ile
        195                 200                 205

Thr Asp Leu Lys Ala Met Leu Thr Leu Gly Thr Leu Thr Phe Gly Met
    210                 215                 220

Gly Val Trp Arg Ile Pro Val Val Gly Leu Ser Ser Leu Ser Gly Glu
225                 230                 235                 240

Gly Phe Glu Glu Leu Ile Asp Lys Ile Ala Ala His Arg Arg Ile Ala
                245                 250                 255

Leu Lys Thr Glu Ala Gly Leu Val Arg Gln Gly Arg Ile Ala Arg Phe
            260                 265                 270

Arg Leu Glu Lys Thr Ala Glu Asn Met Leu Leu Glu Arg Phe Ala Glu
        275                 280                 285

Arg Ala Ala Arg Leu Ala Pro Ser Leu Ala Glu Arg Leu Arg Arg Arg
    290                 295                 300

Asp Gly Asp Pro Tyr Ser Leu Ala Ser Glu Leu Leu Ser Met Pro Val
305                 310                 315                 320

Asp Thr Val Ala Lys Glu Arg Thr His Glu His Val
                325                 330
```

<210> SEQ ID NO 25
<211> LENGTH: 323
<212> TYPE: PRT
<213> ORGANISM: Rhodobacter sphaeroides

<400> SEQUENCE: 25

```
Met Ala Arg Pro Tyr Ile Pro Ser Leu Asp Leu Ile Glu Pro Ala Ala
1               5                   10                  15

Arg Gly Glu Thr Trp Ala Val Ala Arg Leu Ile Ser Arg Ala Glu Ala
            20                  25                  30

Gly Thr Pro Glu Val Arg Glu Ala Ile Gly Glu Ile Tyr Lys Arg Ala
        35                  40                  45

Gly Asn Ala His Val Val Gly Ile Thr Gly Val Pro Gly Ser Gly Lys
    50                  55                  60

Ser Thr Met Val Ser Lys Leu Val Arg Lys Leu Leu Asp Ala Gly Glu
65                  70                  75                  80

Arg Val Ala Val Val Ala Ile Asp Pro Ser Ser Pro Tyr Ser Gly Gly
                85                  90                  95

Ser Ile Leu Gly Asp Arg Ile Arg Met Ser Asp Leu Val Leu Asp Pro
            100                 105                 110

Asn Val Phe Ile Arg Ser Met Ala Thr Arg Gly Ala Val Gly Gly Met
        115                 120                 125

Ala His Ala Ala Leu Asp Val Val Asp Ile Leu Asp Leu Ala Gly Phe
    130                 135                 140

Asp Arg Ile Ile Ile Glu Thr Val Gly Val Gly Gln Asp Glu Val Glu
145                 150                 155                 160

Ile Ala Lys Ala Ser His Thr Thr Val Val Ser Ala Pro Gly Leu
                165                 170                 175

Gly Asp Glu Ile Gln Ala Ile Lys Ala Gly Ile Leu Glu Ile Ala Asp
            180                 185                 190

Leu His Val Val Ser Lys Cys Asp Arg Ser Asp Ala Asn Arg Thr Leu
```

```
                195                 200                 205
Thr Asp Leu Lys Thr Met Leu Lys Asp Gly Leu Gly Ser Ala Leu Thr
210                 215                 220

Arg Gly Trp Leu Pro Pro Val Ile Gly Thr Ser Ser Tyr Asp Asp Gln
225                 230                 235                 240

Gly Phe Glu Asp Leu Ile Ser Gly Phe Ser Arg His Leu Ala His Leu
                245                 250                 255

Asp Gly Pro Ala Gly Ala Arg Arg Glu Gln Ile Ser Val Phe Arg
                260                 265                 270

Leu Lys Lys Ala Ala Glu Ala Leu Met Leu Glu Arg Leu Arg Arg His
275                 280                 285

Pro Ala Phe Glu Pro Glu Gly Arg Arg Val Ala Ala Arg Gln Thr Asp
290                 295                 300

Pro Tyr Ala Ala Ala Ser Gly Ile Val Lys Gln Phe Ser Met Glu Lys
305                 310                 315                 320

Pro His Val

<210> SEQ ID NO 26
<211> LENGTH: 323
<212> TYPE: PRT
<213> ORGANISM: Rhodobacter sphaeroides

<400> SEQUENCE: 26

Met Ala Arg Pro Tyr Ile Pro Ser Leu Asp Leu Ile Glu Pro Ala Ala
1               5                   10                  15

Arg Gly Glu Thr Trp Ala Val Ala Arg Leu Ile Ser Arg Ala Glu Ala
                20                  25                  30

Gly Thr Pro Glu Val Arg Ala Ala Ile Gly Glu Ile Tyr Lys Arg Ala
            35                  40                  45

Gly Asn Ala His Val Val Gly Ile Thr Gly Val Pro Gly Ser Gly Lys
        50                  55                  60

Ser Thr Met Val Ser Lys Leu Val Arg Lys Leu Leu Asp Ala Gly Glu
65                  70                  75                  80

Arg Val Ala Val Val Ala Ile Asp Pro Ser Ser Pro Tyr Ser Gly Gly
                85                  90                  95

Ser Ile Leu Gly Asp Arg Ile Arg Met Ser Asp Leu Val Leu Asp Pro
            100                 105                 110

Asn Val Phe Ile Arg Ser Met Ala Thr Arg Gly Ala Val Gly Gly Met
        115                 120                 125

Ala His Ala Ala Leu Asp Val Val Asp Ile Leu Asp Leu Ala Gly Phe
130                 135                 140

Asp Arg Ile Ile Ile Glu Thr Val Gly Val Gly Gln Asp Glu Val Glu
145                 150                 155                 160

Ile Ala Lys Ala Ser His Thr Thr Val Val Ser Ala Pro Gly Leu
                165                 170                 175

Gly Asp Glu Ile Gln Ala Ile Lys Ala Gly Ile Leu Glu Ile Ala Asp
            180                 185                 190

Leu His Val Val Ser Lys Cys Asp Arg Ser Asp Ala Asn Arg Thr Leu
        195                 200                 205

Thr Asp Leu Lys Thr Met Leu Lys Asp Gly Leu Gly Ser Ala Leu Thr
210                 215                 220

Arg Gly Trp Leu Pro Pro Val Ile Gly Thr Ser Ser Tyr Asp Asp Gln
225                 230                 235                 240

Gly Phe Glu Asp Leu Ile Ser Gly Phe Gly Lys His Leu Ala His Leu
```

```
                     245                 250                 255
Asp Gly Pro Ala Gly Ala Ala Arg Arg Glu Gln Ile Ser Val Phe Arg
            260                 265                 270

Leu Lys Lys Ala Ala Glu Ala Leu Met Leu Glu Arg Leu Arg Arg His
        275                 280                 285

Pro Ala Phe Glu Pro Glu Gly Arg Arg Val Ala Ala Arg Gln Thr Asp
    290                 295                 300

Pro Tyr Ala Ala Ala Ser Gly Ile Val Lys Gln Phe Ser Met Glu Lys
305                 310                 315                 320

Pro His Val

<210> SEQ ID NO 27
<211> LENGTH: 329
<212> TYPE: PRT
<213> ORGANISM: Methylobacterium extorquens

<400> SEQUENCE: 27

Met Ser Ala Thr Leu Pro Asp Met Asp Thr Leu Arg Glu Arg Leu Leu
1               5                   10                  15

Ala Gly Asp Arg Ala Ala Leu Ala Arg Ala Ile Thr Leu Ala Glu Ser
            20                  25                  30

Arg Arg Ala Asp His Arg Ala Ala Val Arg Asp Leu Ile Asp Ala Val
        35                  40                  45

Leu Pro Gln Thr Gly Arg Ala Ile Arg Val Gly Ile Thr Gly Val Pro
    50                  55                  60

Gly Val Gly Lys Ser Thr Thr Ile Asp Ala Leu Gly Ser Leu Leu Thr
65                  70                  75                  80

Ala Ala Gly His Lys Val Ala Val Leu Ala Val Asp Pro Ser Ser Thr
                85                  90                  95

Arg Thr Gly Gly Ser Ile Leu Gly Asp Lys Thr Arg Met Ala Arg Leu
            100                 105                 110

Ala Ile Asp Arg Asn Ala Phe Ile Arg Pro Ser Pro Ser Ser Gly Thr
        115                 120                 125

Leu Gly Gly Val Ala Ala Lys Thr Arg Glu Thr Met Leu Leu Cys Glu
    130                 135                 140

Ala Ala Gly Phe Asp Val Ile Leu Val Glu Thr Val Gly Val Gly Gln
145                 150                 155                 160

Ser Glu Thr Ala Val Ala Asp Leu Thr Asp Phe Phe Leu Val Leu Met
                165                 170                 175

Leu Pro Gly Ala Gly Asp Glu Leu Gln Gly Ile Lys Lys Gly Ile Leu
            180                 185                 190

Glu Leu Ala Asp Met Ile Ala Val Asn Lys Ala Asp Asp Gly Asp Gly
        195                 200                 205

Glu Arg Arg Ala Ser Ala Ala Ser Glu Tyr Arg Ala Ala Leu Arg
    210                 215                 220

Ile Leu Thr Pro Pro Ser Ala Thr Trp Thr Pro Pro Val Thr Ile
225                 230                 235                 240

Ser Gly Leu His Gly Lys Gly Leu Asp Ser Leu Trp Ser Arg Ile Glu
                245                 250                 255

Gly His Arg Ser Lys Leu Thr Ala Thr Gly Glu Ile Ala Gly Lys Arg
            260                 265                 270

Arg Glu Gln Asp Val Lys Trp Met Trp Ala Leu Val His Glu Arg Leu
        275                 280                 285

His Gln Arg Leu Val Gly Ser Ala Glu Val Arg Gln Ala Thr Ala Glu
```

```
            290                 295                 300
Ala Glu Arg Ala Val Ala Gly Gly Glu His Ser Pro Ala Ala Gly Ala
305                 310                 315                 320

Asp Ala Ile Ala Thr Leu Ile Gly Leu
                325

<210> SEQ ID NO 28
<211> LENGTH: 562
<212> TYPE: PRT
<213> ORGANISM: Methylibium petroleiphilum

<400> SEQUENCE: 28

Met Thr Trp Leu Glu Pro Gln Ile Lys Ser Gln Leu Gln Ser Glu Arg
1               5                   10                  15

Lys Asp Trp Glu Ala Asn Glu Val Gly Ala Phe Leu Lys Lys Ala Pro
            20                  25                  30

Glu Arg Lys Glu Gln Phe His Thr Ile Gly Asp Phe Pro Val Gln Arg
        35                  40                  45

Thr Tyr Thr Ala Ala Asp Ile Ala Asp Thr Pro Leu Glu Asp Ile Gly
    50                  55                  60

Leu Pro Gly Arg Tyr Pro Phe Thr Arg Gly Pro Tyr Pro Thr Met Tyr
65                  70                  75                  80

Arg Ser Arg Thr Trp Thr Met Arg Gln Ile Ala Gly Phe Gly Thr Gly
                85                  90                  95

Glu Asp Thr Asn Lys Arg Phe Lys Tyr Leu Ile Ala Gln Gly Gln Thr
            100                 105                 110

Gly Ile Ser Thr Asp Phe Asp Met Pro Thr Leu Met Gly Tyr Asp Ser
        115                 120                 125

Asp His Pro Met Ser Asp Gly Glu Val Gly Arg Glu Gly Val Ala Ile
    130                 135                 140

Asp Thr Leu Ala Asp Met Glu Ala Leu Leu Ala Asp Ile Asp Leu Glu
145                 150                 155                 160

Lys Ile Ser Val Ser Phe Thr Ile Asn Pro Ser Ala Trp Ile Leu Leu
                165                 170                 175

Ala Met Tyr Val Ala Leu Gly Glu Lys Arg Gly Tyr Asp Leu Asn Lys
            180                 185                 190

Leu Ser Gly Thr Val Gln Ala Asp Ile Leu Lys Glu Tyr Met Ala Gln
        195                 200                 205

Lys Glu Tyr Ile Tyr Pro Ile Ala Pro Ser Val Arg Ile Val Arg Asp
    210                 215                 220

Ile Ile Thr Tyr Ser Ala Lys Asn Leu Lys Arg Tyr Asn Pro Ile Asn
225                 230                 235                 240

Ile Ser Gly Tyr His Ile Ser Glu Ala Gly Ser Ser Pro Leu Gln Glu
                245                 250                 255

Ala Ala Phe Thr Leu Ala Asn Leu Ile Thr Tyr Val Asn Glu Val Thr
            260                 265                 270

Glu Thr Gly Met His Val Asp Glu Phe Ala Pro Arg Leu Ala Phe Phe
        275                 280                 285

Phe Val Ser Gln Gly Asp Phe Phe Glu Glu Val Ala Lys Phe Arg Ala
    290                 295                 300

Leu Arg Arg Cys Tyr Ala Lys Ile Met Lys Glu Arg Phe Gly Ala Lys
305                 310                 315                 320

Asn Pro Glu Ser Met Arg Leu Arg Phe His Cys Gln Thr Ala Ala Ala
                325                 330                 335
```

```
Thr Leu Thr Lys Pro Gln Tyr Met Val Asn Val Arg Thr Ser Leu
            340                 345                 350
Gln Ala Leu Ser Ala Val Leu Gly Gly Ala Gln Ser Leu His Thr Asn
        355                 360                 365
Gly Tyr Asp Glu Ala Phe Ala Ile Pro Thr Glu Asp Ala Met Lys Met
    370                 375                 380
Ala Leu Arg Thr Gln Gln Ile Ile Ala Glu Glu Ser Gly Val Ala Asp
385                 390                 395                 400
Val Ile Asp Pro Leu Gly Gly Ser Tyr Tyr Val Glu Ala Leu Thr Thr
                405                 410                 415
Glu Tyr Glu Lys Lys Ile Phe Glu Ile Leu Glu Glu Val Glu Lys Arg
            420                 425                 430
Gly Gly Thr Ile Lys Leu Ile Glu Gln Gly Trp Phe Gln Lys Gln Ile
        435                 440                 445
Ala Asp Phe Ala Tyr Glu Thr Ala Leu Arg Lys Gln Ser Gly Gln Lys
    450                 455                 460
Pro Val Ile Gly Val Asn Arg Phe Val Glu Asn Glu Asp Val Lys
465                 470                 475                 480
Ile Glu Ile His Pro Tyr Asp Asn Thr Thr Ala Glu Arg Gln Ile Ser
                485                 490                 495
Arg Thr Arg Arg Val Arg Ala Glu Arg Asp Glu Ala Lys Val Gln Ala
            500                 505                 510
Met Leu Asp Gln Leu Val Ala Val Ala Lys Asp Glu Ser Gln Asn Leu
        515                 520                 525
Met Pro Leu Thr Ile Glu Leu Val Lys Ala Gly Ala Thr Met Gly Asp
    530                 535                 540
Ile Val Glu Lys Leu Lys Gly Ile Trp Gly Thr Tyr Arg Glu Thr Pro
545                 550                 555                 560
Val Phe

<210> SEQ ID NO 29
<211> LENGTH: 136
<212> TYPE: PRT
<213> ORGANISM: Methylibium petroleiphilum

<400> SEQUENCE: 29

Met Asp Gln Ile Pro Ile Arg Val Leu Leu Ala Lys Val Gly Leu Asp
1               5                   10                  15
Gly His Asp Arg Gly Val Lys Val Val Ala Arg Ala Leu Arg Asp Ala
            20                  25                  30
Gly Met Asp Val Ile Tyr Ser Gly Leu His Arg Thr Pro Glu Glu Val
        35                  40                  45
Val Asn Thr Ala Ile Gln Glu Asp Val Asp Val Leu Gly Val Ser Leu
    50                  55                  60
Leu Ser Gly Val Gln Leu Thr Val Phe Pro Lys Ile Phe Lys Leu Leu
65                  70                  75                  80
Glu Glu Arg Gly Ala Gly Asp Leu Ile Val Ile Ala Gly Gly Val Met
                85                  90                  95
Pro Asp Glu Asp Ala Ala Ala Ile Arg Lys Leu Gly Val Arg Glu Val
            100                 105                 110
Leu Leu Gln Asp Thr Pro Pro Gln Ala Ile Ile Asp Ser Ile Arg Ala
        115                 120                 125
Leu Val Ala Ala Arg Gly Ala Arg
    130                 135
```

USE OF A PROTEIN HOMOLOGOUS TO A MEAB PROTEIN FOR INCREASING THE ENZYMATIC ACTIVITY OF A 3-HYDROXYCARBOXYLIC ACID-COA MUTASE

FIELD OF THE INVENTION

The invention relates to the use of a protein homologous to an MeaB protein for increasing the enzymatic activity of a 3-hydroxycarboxylic acid-CoA mutase, to a fusion protein comprising a 3-hydroxy-carboxylic acid-CoA mutase and a protein sequence homologous to an MeaB protein, and to an enzymatic method for producing 2-hydroxyisobutyric acid.

BACKGROUND OF THE INVENTION

The reactant 2-hydroxyisobutyric acid (2-HIB) can be converted by dehydration to methacrylic acid, a commercially important raw material, whereby industrial applicability is established.

WO 2007/110394 describes a method for enzymatically producing 2-hydroxy-2-methylcarboxylic acids from 3-hydroxycarboxylic acids, wherein a unit having 3-hydroxycarboxylic acid-CoA-mutase activity, which unit has both 3-hydroxycarbonyl-CoA ester-producing and 3-hydroxycarbonyl-CoA ester-isomerizing activities and which causes 3-hydroxycarboxylic acid to be converted to the corresponding 2-hydroxy-2-methylcarboxylic acid, is used. The cobalamine-dependent mutases specified as suitable units having 3-hydroxycarboxylic acid-CoA-mutase activity are those of HCM-10 (DSM 18028), *Methylibium petroleiphilum* PM1, *Methylibium* sp. R8 (strain collection of UFZ Leipzig, Germany), *Xanthobacter autotrophicus* Py2, *Rhodobacter sphaeroides* (ATCC 17029) or *Nocardioides* sp. JS614.

DE102008002715 describes the recombinant use of the 3-hydroxycarboxylic acid-CoA mutases described in WO 2007/110394 for producing 2-hydroxyisobutyric acid in cells which comprise the 2-hydroxy-2-methylcarboxylic acids via the intermediate acetoacetyl-coenzyme A and the precursor 3-hydroxybutyryl-coenzyme A; further, suitable 3-hydroxycarboxylic acid-CoA mutases mentioned there are those which can be isolated from *Aquincola tertiaricarbonis* L108, *Aquincola tertiaricarbonis* DSM 18512, *Marinobacter algicola* DG893, *Sinorhizobium medicae* WSM419, *Roseovarius* sp. 217, *Pyrococcus furiosus* DSM 3638.

A gene coding for the putative protein whose function is still unknown and which is also referred to as MeaB hereinbelow is located in the *A. tertiaricarbonis* genome upstream of the hcmA gene coding for the large subunit of 3-hydroxycarboxylic acid-CoA mutase. Sequence comparisons show homologies to enzymes having an ATPase/GTPase function.

A shared feature of the enzymatic methods described for producing 2-hydroxyisobutyric acid is that of low yields, since the enzymatic turnover rates are low.

It was therefore an object of the invention to provide a method for producing 2-hydroxyisobutyric acid with higher yields.

DESCRIPTION OF THE INVENTION

Surprisingly, the use described hereinbelow of protein sequences homologous to an MeaB protein and the fusion protein described hereinbelow were found to contribute to achieving said object.

The present invention therefore relates to the use of a protein homologous to an MeaB protein for increasing the enzymatic activity of a 3-hydroxycarboxylic acid-CoA mutase. The invention also relates to a fusion protein comprising a 3-hydroxycarboxylic acid-CoA mutase and a protein sequence homologous to an MeaB protein.

The invention also relates to an enzymatic method for producing 2-hydroxyisobutyric acid.

A contribution to achieving the object mentioned at the outset is made by the use of a protein comprising a protein sequence of at least 100, preferably at least 200, in particular at least 300, amino acids, which sequence is homologous to an MeaB protein and has a sequence identity of at least 60%, preferably at least 80%, particularly preferably at least 95%, very particularly preferably at least 99%, in particular 100%, to an MeaB protein, for increasing the enzymatic activity of a 3-hydroxycarboxylic acid-CoA mutase.

A 3-hydroxycarboxylic acid-CoA mutase, abbreviated to Hcm hereinbelow, means an enzyme which catalyzes the reaction of 3-hydroxycarbonyl-CoA esters to give the corresponding 2-hydroxy-2-methylcarboxylic-CoA esters, more specifically of 3-hydroxybutyryl-coenzyme A to give 2-hydroxyisobutyryl-coenzyme A.

The term "MeaB protein" means in the context of the present invention a protein selected from the group of proteins listed by way of accession numbers, consisting of:

SEQ ID NO: 1 (*Aquincola tertiaricarbonis* DSM 18512),
YP_001023545 (SEQ ID NO: 23) (*Methylibium petroleiphilum* PM1),
YP_001409454 (SEQ ID NO: 24) (*Xanthobacter autotrophicus* Py2),
YP_001045518 (SEQ ID NO: 25) (*Rhodobacter sphaeroides* ATCC 17029),
YP_002520048 (SEQ ID NO: 26) (*Rhodobacter sphaeroides*),
AAL86727 (SEQ ID NO: 27) (*Methylobacterium extorquens* AM1),
CAX21841 (*Methylobacterium extorquens* DM4),
YP_001637793 (*Methylobacterium extorquens* PA1),
AAT28130 (*Aeromicrobium erythreum*),
CAJ91091 (*Polyangium cellulosum*),
AAM77046 (*Saccharopolyspora erythraea*), and
NP 417393 (*Escherichia coli* str. K-12 substr. MG1655).

The sequence identities specified are determined by the blastp algorithm, with an expect threshold of 10, a word size of 3, a blosum62 matrix with gap costs of existence: 11 and extension: 1, and a conditional compositional score matrix adjustment.

Protein sequences of at least 100, preferably at least 200, in particular at least 300, amino acids with a sequence identity of at least 60%, preferably at least 80%, particularly preferably at least 95%, very particularly preferably at least 99%, in particular at least 100%, to an MeaB protein are also referred to as "protein sequences homologous to an MeaB protein" hereinbelow.

The terms "2-hydroxyisobutyric acid" and "3-hydroxybutyric acid" mean in particular salts thereof, and also protonated forms, as well as polyhydroxyalkanoates composed of monomers of the respective acid.

All percentages indicated (%) are percentages by mass, unless stated otherwise.

It is obvious to the skilled worker that nucleotide sequences indicated herein or references made herein to specific genes disclosed previously enable probes and primers usable for identifying and/or cloning homologous sequences in other cell types and organisms to be generated in order to identify, for example, further MeaB proteins or hcm which are not explicitly mentioned herein. Such probes and primers usually comprise a nucleotide sequence region which hybridizes under "stringent" conditions (see below) to at least about 12, preferably at least about 25, for example about 40, 50 or 75, contiguous nucleotides of a sense strand of a nucleic acid sequence or of a corresponding antisense strand.

Nucleic acid sequences can be isolated, for example, by customary hybridization methods or the PCR technique from other organisms, for example by way of genomic or cDNA libraries. These DNA sequences hybridize under standard conditions to the specified sequences. Advantageously, short oligonucleotides of the conserved regions, for example of the active site, which can be determined in a manner known to the skilled worker by comparison with a mutase or ATPase/GTPase according to the invention, are used for hybridization. It is also possible, however, to use longer fragments of said nucleic acids or the complete sequences for hybridization. These standard conditions vary depending on the nucleic acid used (oligonucleotide, longer fragment or complete sequence) or depending on which type of nucleic acid, DNA or RNA, is used for hybridization. Thus, for example, the melting temperatures of DNA:DNA hybrids are approx. 10° C. lower than those of DNA:RNA hybrids of the same length.

Depending on the nucleic acid, standard conditions mean, for example, temperatures between 42 and 58° C. in an aqueous buffer solution at a concentration of between 0.1 and 5×SSC (1×SSC=0.15 M NaCl, 15 mM sodium citrate, pH 7.2) or additionally in the presence of 50% formamide, for example 42° C. in 5×SSC, 50% formamide. The hybridization conditions for DNA:DNA hybrids are advantageously 0.1×SSC and temperatures between about 20° C. and 45° C., preferably between about 30° C. and 45° C. The hybridization conditions for DNA:RNA hybrids are advantageously 0.1× SSC and temperatures between about 30° C. and 55° C., preferably between about 45° C. and 55° C. These specified hybridization temperatures are melting temperatures calculated by way of example for a nucleic acid of approx. 100 nucleotides in length, with a G+C content of 50% in the absence of formamide. The experimental conditions for DNA hybridization are described in relevant genetics textbooks such as, for example, Sambrook et al., "Molecular Cloning", Cold Spring Harbor Laboratory, 1989, and can be calculated using formulae known to the skilled worker, for example as a function of the length of the nucleic acids, the type of hybrids or the G+C content.

Stringent conditions in the Northern blot technique, for example, mean using a washing solution, for example 0.1× SSC buffer containing 0.1% SDS (20×SSC: 3M NaCl, 0.3M sodium citrate, pH 7.0) at 50-70° C., preferably 60-65° C., for eluting nonspecifically hybridized cDNA probes or oligonucleotides. In the process, only highly complementary nucleic acids remain bound to one another. Setting stringent conditions is known to the skilled worker and described, for example, in Ausubel et al., Current Protocols in Molecular Biology, John Wiley & Sons, N.Y. (1989), 6.3.1-6.3.6.

The use according to the invention of the protein comprising a protein sequence homologous to an MeaB protein means in particular the use in a microorganism or in a cell extract thereof.

In this context, preference is given to the protein comprising the protein sequence homologous to an MeaB protein being enhanced in the microorganism in comparison with the wild type of said microorganism.

"To be enhanced" also means that the wild type, prior to modification, does not have the protein comprising the protein sequence homologous to an MeaB protein.

Said enhancement is achieved preferably by introducing an exogenous nucleic acid comprising a nucleic acid sequence coding for the protein comprising the protein sequence homologous to an MeaB protein.

Consequently, "wild type" means for the purposes of the present invention the starting microorganism prior to introduction of said exogenous nucleic acid into said microorganism.

Said enhancement can be achieved in principle by increasing the copy number of the gene sequence or gene sequences coding for the protein comprising the protein sequence homologous to an MeaB protein, by using a strong promoter and, where appropriate, by combining these measures.

The exogenous nucleic acid is preferably an expression vector, in particular one that replicates extra-chromosomally, in which a promoter ensures expression of the protein comprising the protein sequence homologous to an MeaB protein.

Preference is also given to the exogenous nucleic acid being able to cause the nucleic acid sequence coding for the protein comprising the protein sequence homologous to an MeaB protein to integrate into the genome of the microorganism. It is conceivable here for expression of the protein comprising the protein sequence homologous to an MeaB protein to be ensured by the organism's own promoters or else for the integrated nucleic acid itself to have a promoter which has an active effect on expression of the protein comprising the protein sequence homologous to an MeaB protein.

Appropriate expression vectors and integration cassettes for the particular target organisms are known to the skilled worker. Alternatively, in the use according to the invention, the protein comprising the protein sequence homologous to an MeaB protein may also be enhanced in a cell extract of a microorganism, for example by directly adding the protein or by adding an in vitro translation mix for said protein to the cell extract.

Enhancement of the protein comprising the protein sequence homologous to an MeaB protein in comparison with the wild type may be determined by conventional methods. The protein concentration may thus be analyzed by Western blot hybridization using an antibody specific for the protein to be detected (Sambrook et al., *Molecular Cloning: a laboratory manual*, 2$^{nd}$ Ed. Cold Spring Harbor Laboratory Press, Cold Spring Harbor, N.Y. USA, 1989) and subsequent optical evaluation using appropriate software for concentration determination (Lohaus and Meyer (1989) *Biospektrum*, 5: 32-39; Lottspeich (1999), *Angewandte Chemie* 111: 2630-2647).

With the use according to the invention in a microorganism or in a cell extract thereof, preference is given to said microorganism and also, as described above for the protein comprising the protein sequence homologous to an MeaB protein, the 3-hydroxycarboxylic acid-CoA mutase being enhanced. The same applies to the enhancement of said protein in the cell extract.

In this connection, preferred microorganisms are those which are described below in connection with the method according to the invention for producing 2-hydroxyisobutyric acid.

Preference is given according to the invention to using 3-hydroxycarboxylic acid-CoA mutases which can be isolated from the microorganisms selected from the group comprising, in particular consisting of, *Aquincola tertiaricarbonis* L108, *Aquincola tertiaricarbonis* DSM 18028, *Aquincola tertiaricarbonis* DSM 18512, *Methylibium petroleiphilum* PM1, *Methylibium* sp. R8, *Xanthobacter autotrophicus* Py2, *Rhodobacter sphaeroides* ATCC 17029, *Nocardioides* sp. JS614, *Marinobacter algicola* DG893, *Sinorhizobium medi-* cae WSM419, *Roseovarius* sp. 217, *Pyrococcus furiosus* DSM 3638, *Streptomyces cinnamonensis* and *Streptomyces coelicolor*, with particular preference being given to the coenzyme B12-dependent mutases described in PCT/EP2007/052830.

Preferred 3-hydroxycarboxylic acid-CoA mutases can be found in the database of the National Center for Biotechnology Information under accession numbers ABM97311 (SEQ ID NO: 28) and ABM97308.1 (SEQ ID NO: 29) (*M. petroleiphilum* PM1)

YP_001045519 and YP_001045516 (*Rhodobacter sphaeroides* ATCC 17029)

YP_001409455 and YP_001409452 (*Xanthobacter autotrophicus* Py2)

YP_923327 and YP_923324 (*Nocardioides* sp. JS614)

YP_001313797 and YP_001313799 (*Sinorhizobium medicae* WSM419)

ZP_01035346 and ZP_01035348 (*Roseovarius* sp. 217)

NP_579206 (*Pyrococcus furiosus* DSM 3638)

ZP_01892066 and ZP_01892069 (*Marinobacter algicola* DG893)

AAC08713 and CAB59633 (*Streptomyces cinnamonensis*),

CAB40912 and NP_628957 (*Streptomyces coelicolor* A3(2)), and in particular SEQ ID NO: 21 and SEQ ID NO: 22 (incompletely listed as ABD93936 (SEQ ID NO: 28) and ABD93937 (SEQ ID NO: 29), *A. tertiaricarbonis* DSM 18512).

3-Hydroxycarboxylic acid-CoA mutases preferred according to the invention in this connection have a sequence identity to the amino acid sequence of the small and large subunits of the mutase described in PCT/EP2007/052830 (SEQ ID NO: 21 and SEQ ID NO: 22) of at least 60%, preferably at least 80%, particularly preferably at least 95%, very particularly preferably at least 99%, in particular 100%, at the amino acid level.

Preference is given according to the invention to the protein sequence homologous to an MeaB protein being derived from the group consisting of:

SEQ ID NO: 1 (*Aquincola tertiaricarbonis* DSM 18512),

YP_001023545 (SEQ ID NO: 23) (*Methylibium petroleiphilum* PM1),

YP_001409454 (SEQ ID NO: 24) (*Xanthobacter autotrophicus* Py2),

YP_001045518 (SEQ ID NO: 25) (*Rhodobacter sphaeroides* ATCC 17029),

YP_002520048 (SEQ ID NO: 26) (*Rhodobacter sphaeroides*),

AAL86727 (SEQ ID NO: 27) (*Methylobacterium extorquens* AM1).

Particular preference is given according to the invention to the protein sequence homologous to MeaB comprising the same number of amino acids as the relevant MeaB protein itself.

Preference is given according to the invention to using the proteins comprising a protein sequence homologous to an MeaB protein by way of fusion proteins according to the invention which are described hereinbelow and which result in an increase in the enzymatic activity of the 3-hydroxycarboxylic acid-CoA mutases.

A further contribution to achieving the object mentioned at the outset is therefore made by a fusion protein comprising a 3-hydroxycarboxylic acid-CoA mutase and a protein sequence of at least 100, preferably at least 200, in particular at least 300, amino acids with a sequence identity of at least 60%, preferably at least 80%, particularly preferably at least 95%, very particularly preferably at least 99%, in particular 100%, to an MeaB protein.

The term "fusion protein" means according to the invention that at least one polypeptide strand which is essential for 3-hydroxycarboxylic acid-CoA-mutase activity contains an additional protein sequence which has the required sequence identities to an MeaB protein. Since 3-hydroxycarboxylic acid-CoA mutases may be oligomeric proteins, the term "fusion protein" therefore likewise means a protein complex which is composed of, for example, a plurality of different subunits of 3-hydroxycarboxylic acid-CoA mutase, with one of said subunits additionally having the MeaB-homologous amino acid sequence. Preferably, the fusion protein according to the invention is an isolated fusion protein.

Preference is given to the fusion protein according to the invention comprising 3-hydroxycarboxylic acid-CoA mutases which are preferred in connection with the above-mentioned use according to the invention; the same applies to protein sequences homologous to an MeaB protein which are preferably present according to the invention described herein.

The protein sequence homologous to MeaB proteins may be arranged in the fusion protein in such a way that it is arranged immediately upstream ("N-terminally") of the 3-hydroxycarboxylic acid-CoA mutase or, in the case of an oligomeric 3-hydroxycarboxylic acid-CoA mutase, immediately upstream of a subunit of said 3-hydroxy-carboxylic acid-CoA mutase, or else downstream ("C-terminally") of the 3-hydroxycarboxylic acid-CoA mutase or of one of its subunits.

Preference is given to the protein sequence homologous to MeaB proteins being N-terminally fused to the 3-hydroxy-carboxylic acid-CoA mutase, preferably to the large subunit of the 3-hydroxycarboxylic acid-CoA mutase.

Additional amino acids may be present between the protein sequence homologous to MeaB proteins and the 3-hydroxycarboxylic acid-CoA mutase. Such "linkers" may be advantageous in that they can affect the three-dimensional arrangement of the proteins. Linkers located between the protein sequence homologous to MeaB proteins and the 3-hydroxycarboxylic acid-CoA mutase have from 4 to 20, preferably 6 to 12, in particular 8, amino acids. A linker consisting of the amino acid sequence Cys Ala Gly Ser Phe Pro Thr Ile, SEQ ID NO: 2, has proved to be particularly advantageous.

A fusion protein preferred according to the invention is characterized by a 3-hydroxycarboxylic acid-CoA mutase selected from the group consisting of SEQ ID: NOS 21 and 22 (*A. tertiaricarbonis* DSM 18512) and ABM97311 (SEQ ID NO: 28) and ABM97308.1 (SEQ ID NO: 29) (*M. petroleiphilum* PM1), and, to the large subunit of which a protein sequence is N-terminally fused which is homologous to MeaB proteins, which sequence can be derived from the group consisting of SEQ ID NO: 1 (*A. tertiaricarbonis* DSM 18512), YP_001023545 (SEQ ID NO: 23) (*M. petroleiphilum* PM1), with the linker consisting of the amino acid sequence Cys Ala Gly Ser Phe Pro Thr Ile (SEQ ID NO: 2).

More specifically, a preferred fusion protein is characterized by a heterodimeric protein comprising, in particular consisting of, SEQ ID NO: 3 and SEQ ID NO: 4.

Molecular biology methods of generating appropriate nucleic acid constructs coding for fusion proteins according to the invention are known to the skilled worker and can be found, for example, in the standard work "*Molecular Cloning: A Laboratory Manual*" (Third Edition) by Joseph Sambrook et al. Thus it is possible, for example via PCR methods, for the nucleic acids coding for protein segments to be fused to be amplified, to be provided with endonuclease cleavage sites and to be ligated by combining appropriate restriction and ligation. Alternatively, it is possible to generate nucleic acids, for example, by SOE-PCR (splicing by overlap extension—polymerase chain reaction), which fuse the two coding genes and, for example, additionally determine the length of the linker.

Nowadays, as a matter of simplification, such nucleic acids are already synthesized artificially by commercial service providers, with the possibility of already optimizing the codon usage with regard to the organism to be used.

A further contribution to achieving the object mentioned at the outset is therefore made by isolated nucleotide sequences (single- and double-stranded DNA and RNA sequences such as, for example, DNA, cDNA and mRNA) coding for fusion proteins according to the invention.

"Coding for" here means the genetic code with a codon usage as can be found, for example, in *E. coli*; however, situations in which an unconventional codon usage such as, for example, in *Tetrahymena, Plasmodium, Mycobacterium pneumoniae* or *Candida tropicalis*, can result in fusion proteins according to the invention are also conceivable. These nucleic acids are also considered to be "coding for fusion protein according to the invention".

Nucleic acids preferred according to the invention code for fusion proteins preferred according to the invention.

More specifically, particular preference is given to a nucleic acid having the SEQ ID NO: 5.

The invention furthermore comprises the nucleic acid molecules complementary to the nucleotide sequences described.

A further contribution to achieving the object stated above is made by a method for enzymatically producing 2-hydroxyisobutyric acid, comprising the method steps of:

a) contacting a1) a microorganism or a cell extract of said microorganism having an enzymatic activity of a 3-hydroxycarboxylic acid-CoA mutase, wherein the protein comprising a protein sequence homologous to an MeaB protein is enhanced in the microorganism or in the cell extract itself in comparison with the wild type of said microorganism, or a2) a entity having a fusion protein according to the invention with an aqueous medium containing 3-hydroxybutyric acid, and, where appropriate, b) purifying the 2-hydroxyisobutyric acid from the aqueous medium or from the entity having the fusion protein.

It is obvious that it is also possible to employ mixtures of various microorganisms or extracts thereof according to a1), mixtures of various entities having fusion protein according to the invention according to a2), and also combinations thereof.

The entity having a fusion protein in a2) is preferably a microorganism or a cell extract thereof.

Usually, said microorganism has been genetically modified in such a way that it itself produces fusion protein according to the invention. Said modification is carried out, for example, by transforming said microorganism with an expression vector which comprises nucleic acid according to the invention.

Suitable microorganisms in a1) or a2) are bacteria, yeasts or fungi, more specifically those bacteria, yeasts or fungi which have been deposited with the Deutsche Sammlung von Mikroorganismen and Zellkulturen [German Collection of Microorganisms and Cell Cultures] GmbH (DSMZ), Brunswick, Germany, by way of bacteria, yeast or fungal strains.

Microorganisms preferred according to the invention in a1) or a2) are those of the genera *Aspergillus, Corynebacterium, Brevibacterium, Bacillus, Acinetobacter, Alcaligenes, Lactobacillus, Paracoccus, Lactococcus, Candida, Pichia, Hansenula, Kluyveromyces, Saccharomyces, Escherichia, Zymomonas, Yarrowia, Methylobacterium, Ralstonia, Pseudomonas, Rhodospirillum, Rhodobacter, Burkholderia, Clostridium* and *Cupriavidus*, and acetogenic microorganisms, with particular preference being given to *Aspergillus nidulans, Aspergillus niger, Alcaligenes latus, Bacillus megaterium, Bacillus subtilis, Brevibacterium flavum, Brevibacterium lactofermentum, Escherichia coli, Saccharomyces cerevisiae, Kluveromyces lactis, Candida blankii, Candida rugosa, Corynebacterium glutamicum, Corynebacterium efficiens, Zymomonas mobilis, Yarrowia lipolytica, Hansenula polymorpha, Methylobacterium extorquens, Ranstonia eutropha, Thermoanaerobacter kivui, Acetobacterium woodii, Acetoanaerobium notera, Clostridium aceticum, Butyribacterium methylotrophicum, Clostridium acetobutylicum, Moorella thermoacetica, Eubacterium limosum, Peptostreptococcus productus, Clostridium ljungdahlii,* and *Clostridium carboxidivorans*, in particular *Ralstonia eutropha* H16, *Ralstonia eutropha* H16 PHB-4, *Rhodospirillum rubrum, Rhodobacter sphaeroides, Paracoccus versutus, Pseudomonas aeruginosa, Pseudomonas putida, Acinetobacter calcoaceticus,* and *Pichia pastoris*.

The microorganism in a1) or a2) is capable of synthesizing preferably 3-hydroxybutyric acid from carbon sources. Suitable microorganisms supplying 3-hydroxybutyric acid are in particular those described in WO 2007/110394 and DE102008002715. DE102008002715, in particular, contains instructions regarding the means by which the skilled worker can increase the yield of 3-hydroxybutyric acid from carbon sources using recombinant methods.

Examples of carbon sources which may be used are carbohydrates [such as, for example, monosaccharides (e.g. glucose, fructose, galactose, arabinose, xylose), oligosaccharides (e.g. maltose, sucrose, lactose) and polysaccharides (e.g. starch, hydrolyzed starch, cellulose, hydrolyzed cellulose, hemicellulose, hydrolyzed hemicellulose)], and reaction products thereof such as, for example, sugar alcohols and polyhydroxy acids;

carbon dioxide, carbon monoxide, waste gas or syngas;

organic mono-, di- and tricarboxylic acids optionally carrying one or more, e.g. 1, 2, 3 or 4, hydroxyl groups, e.g. acetic acid, tartaric acid, itaconic acid, succinic acid, propionic acid, lactic acid, 3-hydroxypropionic acid, fumaric acid, maleic acid, 2,5-furan-dicarboxylic acid, glutaric acid, levulinic acid, gluconic acid, aconitic acid, succinic acid, and diaminopimelic acid, citric acid;

lipids;

oils or fats such as, for example, rapeseed oil, soya oil, palm oil, sunflower oil, peanut oil, and coconut oil;

saturated and unsaturated fatty acids with preferably from 10 to 22 carbons, for example γ-linolenic acid, dihomo-γ-linolenic acid, arachidonic acid, palmitic acid, stearic acid, oleic acid, lauric acid, linoleic acid, eicosapentaenoic acid, and docosahexaenoic acid;

hydrocarbons, for example with from 1 to 22 carbons containing one or more double or triple bonds, such as methane, ethane, ethene, ethylene, dodecane, octadecane;

alcohols, for example with from 1 to 22 carbons, e.g. butanol, methanol, ethanol;

diols with preferably from 3 to 8 carbons, e.g. propanediol and butanediol;

polyhydric (also referred to as higher) alcohols with 3 or more, for example 3, 4, 5 or 6, OH groups, e.g. glycerol, sorbitol, mannitol, xylitol, and arabinitol;

ketones with preferably from 3 to 10 carbons and optionally 1 or more hydroxyl groups, e.g. acetone and acetoin;

lactones, e.g. γ-butyrolactone, cyclodextrins, biopolymers, e.g. polyhydroxyacetate, polyesters, e.g. polylactide, polysaccharides, polyisoprenoids, polyamides;

aromatic compounds, e.g. aromatic amines, vanillin and indigo;

proteins, for example enzymes such as amylases, pectinases, acidic, hybrid or neutral cellulases, esterases such as lipases, pancreases, proteases, xylanases, and oxidoreductases such as laccase, catalase, and peroxidase, glucanases, phytases;

carotenoids, e.g. lycopene, β-carotene, astaxanthin, zeaxanthin, and canthaxanthin;

proteinogenic and non-proteinogenic amino acids, e.g. lysine, glutamate, methionine, phenylalanine, aspartic acid, tryptophan, and threonin;

purine and pyrimidine bases;

nucleosides and nucleotides, e.g. nicotinamide adenine dinucleotide (NAD) and adenosine 5'-monophosphate (AMP);

and also precursors and derivatives, for example salts in the case of the acids mentioned, of the compounds mentioned above.

These substances may be used individually or in the form of a mixture. Particular preference is given to using carbohydrates, in particular monosaccharides, oligosaccharides or polysaccharides, as described in U.S. Pat. No. 6,136,576, for example, $C_5$ sugars or glycerol. A preferred alcohol to be used is methanol, since it can be prepared from many different sources such as, for example, biogas, biomass, natural gas or coal.

The carbon sources may be used in different forms (pure Or in solution/suspension) and in different compositions (purified or as crude product) from different processing stages (e.g. sugarcane juice, syrup, molasses, unrefined sugar, refined sugar; corn kernels, flour, starch, dextrin, glucose), before or after treatment (steam explosion, pretreatment with acid, pretreatment with enzyme).

In a preferred, alternative embodiment of the method according to the invention, the carbon source from which 3-hydroxybutyric acid is synthesized comprises $CO_2$ or $CO$, in particular syngas or waste gas. The microorganisms employed in this connection in a1) or a2) are acetogenic microorganisms such as, for example, species of the genus *Acetobacterium*, such as *A. woodii* and *Clostridium aceticum*. More specifically, the acetogenic cells are selected from the group comprising, in particular consisting of, *Acetoanaerobium notera, Acetobacterium woodii, Archaeoglobus fulgidus, Butyribacterium methylotrophicum, Butyribacterium methyltrophicum, Carboxydibrachium pacificus, Carboxydocella sporoproducens, Carboxydocella thermoautotrophica, Carboxydothermus hydrogenoformans, Citrobacter* sp. Y19, *Clostridium aceticum, Clostridium acetobutylicum, Clostridium autoethanogenum, Clostridium carboxidivorans, Clostridium ljungdahlii, Desulfotomaculum carboxydivorans, Desulfotomaculum kuznetsovii, Desulfotomaculum thermobenzoicum* subsp. *thermosyntrophicum, Eubacterium limosum, Methanosarcina acetivorans* C2A, *Methanosarcina barkeri, Methanothermobacter thermoautotrophicus, Moorella* AMP, *Moorella thermoacetica, Moorella thermoautotrophica, Oxobacter pfennigii, Peptostreptococcus productus, Rhodopseudomonas palustris* P4, *Rhodospirillum rubrum, Rubrivivax gelatinosus, Thermincola carboxydiphila, Thermincola ferriacetica, Thermococcus* AM4, *Thermolithobacter carboxydivorans*, and *Thermoanaerobacter kivui*. A particularly suitable cell in this connection is *Clostridium carboxidivorans*, in particular such strains as "P7" and "P11". Such cells are described, for example, in US 2007/0275447 and US 2008/0057554. Another, particularly suitable cell in this connection is *Clostridium ljungdahlii*, in particular strains selected from the group comprising, in particular consisting of, *Clostridium ljungdahlii* PETC, *Clostridium ljungdahlii* ERI2, *Clostridium ljungdahlii* C01, and *Clostridium ljungdahlii* O-52, which are described in WO 98/00558 and WO 00/68407.

Preference is given to a method according to the invention, in which synthesis of 3-hydroxybutyric acid from the carbon source and of 2-hydroxyisobutyric acid from 3-hydroxybutyric acid is carried out in a single method step.

The entity having a fusion protein, which is employed in the method according to the invention, may also be introduced to the reaction in the form of an extract of the microorganism, thus in a form which has been purified, concentrated and/or isolated from said microorganism.

Therefore, for the purposes of the invention, the unit having a fusion protein may be employed in the method according to the invention by way of catalysts, both in the form of intact microorganisms and in the form of permeabilized microorganisms. Further possible uses are in the form of components (one or more) from microbial cell extracts, but also in a partially purified or purified form. Where appropriate, CoA ester-synthesizing enzymes, for example CoA transferase or CoA synthetases, are used according to the invention. The enzymatic catalysts may be immobilized or may be attached to a dissolved or undissolved support material.

In a preferred variant embodiment, particular cell compartments or parts thereof are separated from one another or combined, i.e. carbohydrate structures, lipids or proteins and/or peptides and also nucleic acids, which are capable of beneficially or adversely affecting the activity of the entity having the fusion protein, may be combined or separated. In order to deliberately utilize such influences, crude extracts, for example, are expertly prepared from the microorganisms and, where appropriate, centrifuged in order to be able to carry out a reaction according to the invention with the pellet or the supernatant.

The 2-hydroxyisobutyric acid obtained by the method according to the invention may, depending on the conditions, be in the form of its salts or else in the form of a polyhydroxyalkanoate in which said 2-hydroxyisobutyric acid is stored as functional monomer.

The 2-hydroxyisobutyric acid produced according to the invention may be isolated by subjecting the aqueous medium to already known methods, after undissolved components such as microbial cells have been removed. Such methods are inter alia concentration, ion exchange, distillation, electrodialysis, extraction and crystallization, for example. The product may be isolated as salt or (after acidification) as protonated 2-hydroxyisobutyric acid.

Methods of isolation are known per se to the skilled worker who can find detailed and special instructions in DE102008002715.

The 2-hydroxyisobutyric acid obtained by the method according to the invention may advantageously be used for producing methacrylic acid, methacrylic esters or polymers thereof by means of dehydration and, where appropriate, esterification and, where appropriate, polymerization.

Methods of dehydration, esterification and polymerization are known per se to the skilled worker who can find detailed and special instructions in DE102008002715.

The present invention is described by way of example in the examples hereinbelow but shall not be limited to the embodiments mentioned in said examples, with its range of applications arising from the entire description and the claims.

BRIEF DESCRIPTION OF THE FIGURES

The following figures are part of the examples.

EXAMPLES

1. Isolation of Genomic DNA and Amplification of the Mutase Operon Including the Genes hcmB, hcl, meaB and hcmA Genomic DNA was isolated from the strain *Aquincola tertiaricarbonis* DSM 18512 using the DNeasy Blood & Tissue Kit (Qiagen GmbH, Hilden, Germany) according to the manufacturer's information and used as template in a PCR for amplifying the mutase operon. The primers were derived from the sequence of the organism *Methylibium petroleiphilum* PM1 plasmid RPME01 (NCBI Accession: CP000556.1), since the nucleotide sequence of the genes in the operon, hcmA (icmA) and hcmB (icmB) is >97% similar to those of *Aquincola tertiaricarbonis* DSM 18512. The oligonucleotides UPicmB_fw 5'-CAGCGACTTGCAACCTTCT-TCACCGG-3' (forward primer, SEQ ID NO: 8) and ICM5,4-PMI_rev 5'-GTATCAGTCGCTCCGACTTGCCGATCC-3' (reverse primer, SEQ ID NO: 9) were used here for amplifying the genes located inbetween.

The polymerase chain reaction (PCR, according to SAIKI et al., 1985, Enzymatic amplification of β-globin genomic sequences and restriction site analysis for diagnosis of sickle cell anemia. Science 230:1350-1354.) mix included Pfu polymerase (Promega, Madison, USA). The PCR comprised 35 cycles of in each case 60 seconds at 95° C., 30 seconds at 65° C. and 8 minutes at 72° C. and was carried out in a thermocycler (Primus 96 advanced; PEQLAB Biotechnologie GmbH, Erlangen, Germany).

The fragments were purified using the QIAquick PCR Purification Kit (Qiagen GmbH, Hilden) according to the manufacturer's information.

2. Preparation of a *Ralstonia eutropha* Expression Vector

The purified PCR fragment "Mutase-Operon" (approx. 5.4 kbp) was ligated into the vector pET101/D-TOPO (Invitrogen GmbH, Karlsruhe, Germany) according to the manufacturer's information. The resulting hybrid plasmid, pET101/D-TOPO::Mutase-Operon, was transferred into competent *E. coli* DH5α cells (New England Biolabs, Frankfurt, Germany) and checked by restriction and sequencing.

In addition, the PCR product was cloned into the plasmid pCR-BluntIITOPO (Invitrogen GmbH, Karlsruhe) according to the manufacturer's information. The hybrid plasmid obtained, pCR-BluntIITOPO::Mutase-Operon, was transferred into competent *E. coli* DH5α cells (New England Biolabs, Frankfurt) and checked by restriction and sequencing.

To obtain expression in *R. eutropha* strains, the construct had to be cloned into a suitable broad-host-range vector. The vector used is pBBR1MCS-2, described in KOVACH et al. (1995). Four new derivatives of the broad-host-range cloning vector pBBR1MCS carrying different antibiotic-resistance cassettes. Gene, 166:175-176.

Figure 1:
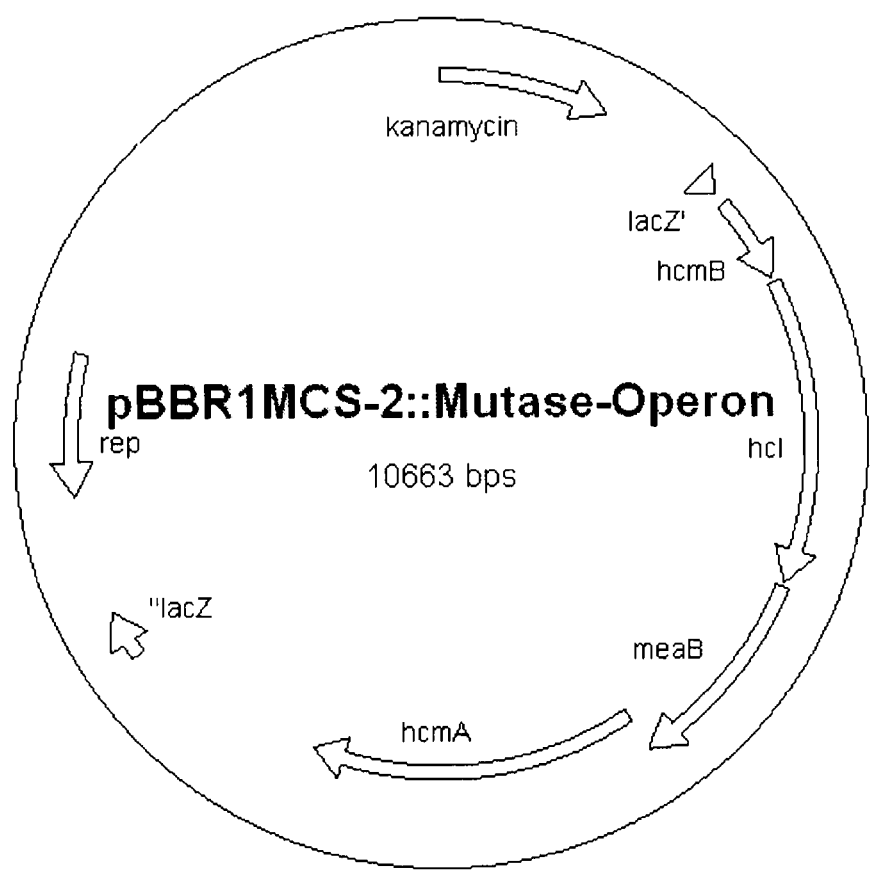
FIG. 1: Hybrid plasmid pBBR1MCS-2::Mutase-Operon

For this purpose, the plasmids pCR-BluntIITOPO::Mutase-Operon and pBBR1MCS-2 were digested with the enzymes EcoRV and SpeI, and the Mutase-Operon fragment was ligated into the pBBR1MCS-2 target vector, and competent *E. coli* DH5α cells (New England Biolabs, Frankfurt) were transformed with the resultant hybrid plasmid, pBBR1MCS-2::Mutase-Operon (FIG. 1, sequence ID No. 6).

The plasmid was checked by restriction and sequencing and introduced by means of electroporation (2.43 kV, 25 µF, 200Ω) into competent *R. eutropha* H 16 PHB-4 (reclassified as *Cupriavidus necator*, DSM 541). Transformants were obtained which harbor the pBBR1MCS-2::Mutase-Operon plasmid.

To delete the hcl gene which codes for a putative 2-HIB-CoA ligase, a mutation PCR with subsequent fusion PCR was carried out.

The following primers were utilized for the mutation PCR:
Fragment A (1228_pCOLAD_fp1×1251_hcl_de1−) was amplified using the primers 1228_pCOLAD_fp1: 5'-GGA ATT GTG AGC GGA TAA-3' SEQ ID NO: 10 and 1251_hcl_del−: 5'-CAG CGC CCC GGG ATA CTC GAC CGG AAA GTT CC-3' SEQ ID NO: 11, Fragment B (1251_hcl_del+x 1251_nach_stuI) was amplified using the primers 1251_hcl_del+5'-GAG TAT CCC GGG GCG CTG AAC CAG CAA CTG-3' SEQ ID NO: 12 and 1251_nach_StuI5'-ATG GCC TGG ATC TCG TCT C-3' SEQ ID NO: 13.

Figure 2:
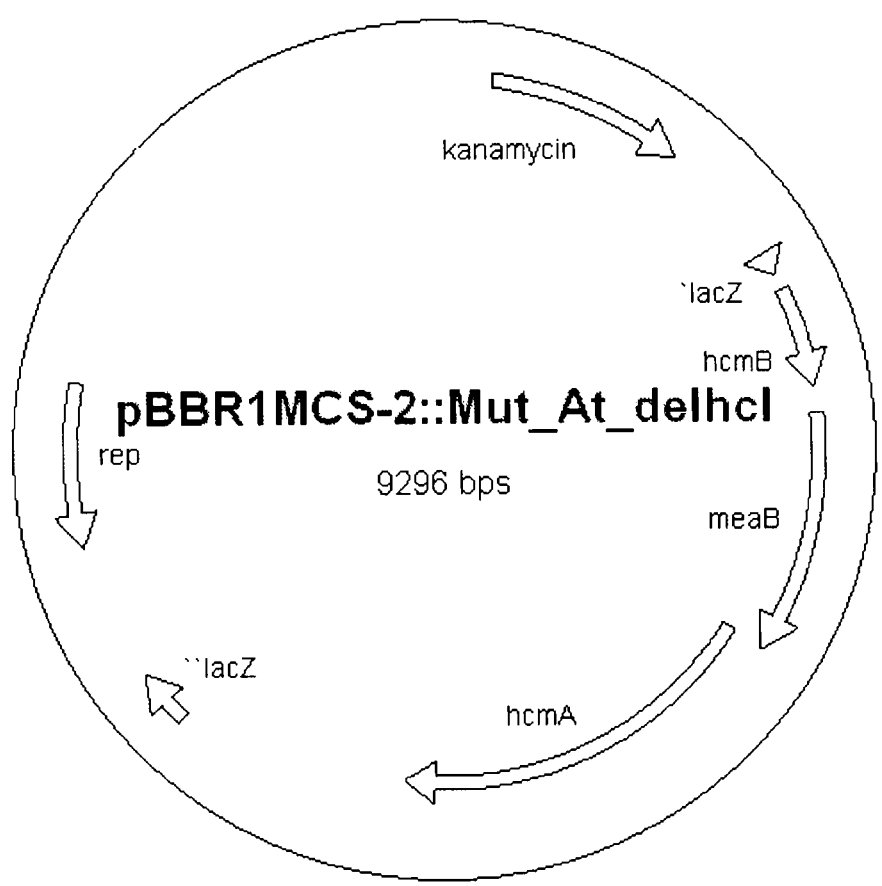
FIG. 2: Hybrid plasmid pBBR1MCS-2::Mut_At_delhcl.

The fusion PCR (see above: 35 cycles of in each case 60 seconds at 95° C., 30 seconds at 65° C. and 7 minutes at 72° C.) was carried out using the primers 1228_pCOLAD_fp1 and 1251_nach_StuI and the PCR product was cloned via HindIII/StuI back into the starting vector pBBR1MCS-2. The resultant hybrid plasmid, pBBR1MCS-2::Mut_At_delhcl (FIG. 2), was checked by restriction and sequencing.

3. Amplification of Fragments hcmA, meaB and hcmB; Fusion of the Coding Regions of MeaB (N-Terminally) and HcmA (C-Terminally)

The plasmid described in example 2, pBBR1MCS-2::Mut_At_delhcl, was used as template for a PCR for amplifying the fragments hcmA (1.7 kbp; DQ436456), hcmB (0.4 kbp; DQ436457) and the fragment referred to as meaB (1 kbp).

Fusion of the coding regions of MeaB (N-terminally) and HcmA (C-terminally) requires the hcmA start codon and the meaB stop codon to be modified. The oligonucleotides MeaB_NsiI_fw 5'-ATAGCA ATGCATGACCGGAATGACTTACGTTCCC-3' (forward primer; NsiI cleavage site is underlined; start codon is emboldened, SEQ ID NO: 14) and MeaBFus_HindIII_rev 5'-ACTTTAAGCTTGGCGCAAGCCAGGTCATTCG-3'

(reverse primer; HindIII-cleavage site is underlined; modified stop codon is emboldened, SEQ ID NO: 15) were used for amplification of meaB (1 kbp).

Amplification of hcmA (1.7 kbp) was carried out using the primer hcmAFus_HindIII_fw 5'-AAA AAGCTTACCATAACCTGGCTTGAGCCG-3' (HindIII cleavage site is underlined; modified start codon is emboldened, SEQ ID NO: 16) and the primer hcmA_SpeI_rev 5'-ATACCGACTAGTGCTCAGAAGACCGGCGTCTC-3' (SpeI cleavage site is underlined; stop codon is emboldened, SEQ ID NO: 17).

The hcmB fragment (0.5 kbp) was amplified using the oligonucleotides hcmB_SpeI_fw 5'-AAATCT ACTAGTTGGAGATCCCACCATGGACCAAATCCCG-3' (forward primer; SpeI cleavage site is underlined; start codon is emboldened, SEQ ID NO: 18) and hcmB_SacI_rev 5'-TAGGCT GAGCTCCAAGCTTCGAATTGAGCTCGCCCTTTCAG-3' (reverse primer; SacI cleavage site is underlined; stop codon is emboldened, SEQ ID NO: 19).

The polymerase chain reaction (PCR, according to SAIKI et al., 1985, Enzymatic amplification of β-globin genomic sequences and restriction site analysis for diagnosis of sickle cell anemia. Science 230:1350-1354.) mix was prepared using the Phusion™ High-Fidelity PCR Master Mix (Finnzymes, Espoo, Finland). After the initial denaturation (30 s; 98° C., 35 cycles of in each case 10 s at 98° C.), 30 s at 65° C. and 1 min at 72° C. were carried out. The mixtures were incubated for 10 min at 72° C. for the final elongation. The PCR was carried out in a thermocycler (Primus 96 advanced; PEQLAB Biotechnologie GmbH, Erlangen).

The PCR mixtures were fractionated by means of gel electrophoresis, the 1 kbp meaB fragment was isolated from the gel, purified using the QIAquick Gel Extraction Kit (Qiagen GmbH, Hilden) according to the manufacturer's information and then digested with NsiI and HindIII. The 1.7 kbp hcmA fragment was purified directly from the PCR mixture by means of the QIAquick PCR Purification Kit (Qiagen GmbH, Hilden) according to the manufacturer's information and digested with HindIII and SpeI. Both mixtures were ligated using the HindIII cleavage site.

The ligation product, meaBhcmA (2.7 kbp), was used as template for an SOE-PCR using the oligonucleotides MeaB_NsiI_fw 5'-ATAGCA ATGCATGACCGGAATGACTTACGTTCCC-3' (NsiI cleavage site is underlined; start codon is emboldened, SEQ ID NO: 14) and hcmA_Spd_rev 5'-ATACCG ACTAGTGCTCAGAAGACCGGCGTCTC-3' (SpeI-cleavage site is underlined; stop codon is emboldened, SEQ ID NO: 17) (initial denaturation: 30 s, 98° C.; 35 cycles of in each case 10 s at 98° C., 30 s at 65° C. and 1 min at 72° C.; final elongation: 10 min at 72° C.). The resulting PCR product of the appropriate size was fractionated by means of gel electrophoresis, isolated and purified using the QIAquick Gel Extraction Kit (Qiagen GmbH, Hilden).

Following the PCR, the hcmB fragment was purified using the QIAquick PCR Purification Kit (Qiagen GmbH, Hilden) and digested with SpeI and SacI.

4. Preparation of a *Ralstonia eutropha* Expression Vector

The purified meaBhcmA-fusion fragment (2.7 kbp) was ligated into the broad-host-range vector pBBR1MCS-2 which had likewise been digested with these two restriction endonucleases. The resulting hybrid plasmid, pBBR1MCS-2::meaBhcmA was transferred into competent *E. coli* DH5α cells (New England Biolabs, Frankfurt) and checked by restriction and sequencing. In addition, hcmB was cloned into the vector. For this purpose, the pBBR1MCS-2::meaBhcmA vector was digested with SpeI and SacI. The purified hcmB fragment was ligated into said vector and an aliquot of the ligation mixture was then transferred into DH5α cells (New England Biolabs, Frankfurt). The resulting hybrid plasmid, pBBR1MCS-2::meaBhcmA-hcmB-P, was checked by restriction and sequencing.

NsiI had to be used as cleavage site for generating the hybrid plasmid, owing to the numerous unique cleavage sites present in the inserts of pBBR1MCS-2 and, in contrast, the few remaining unique cleavage sites in the multiple cloning site (MCS) of pBBR1MCS-2. The NsiI cleavage site is located upstream of the promoter region, and, as a result, the promoter was removed from the vector during cloning. To enable transcription, the entire construct, meaBhcmA-hcmB-P (3.1 kbp), was amplified using the oligonucleotides MeaB_RBS_fw 5'-AAATTTAGATCTGGAGACCGGAAT-GACTTACGTTCCC-3' (start codon is emboldened, SEQ ID NO: 20) and hcmB_SacI_rev 5'-TAGGCT GAGCTCCAAGCTTCGAATTGAGCTCGCCCTTTCAG-3' (SacI cleavage site is underlined; stop codon is emboldened, SEQ ID NO: 19) in a PCR provided by means of Phusion™ High-Fidelity PCR Master Mix (Finnzymes, Espoo, Finland) (initial denaturation: 30 s, 98° C.; 35 cycles of in each case 10 s at 98° C., 30 s at 65° C. and 1 min at 72° C.; final elongation: 10 min at 72° C.). The PCR product was purified and, like the empty pBBR1MCS-2 vector, digested with EcoRV and SacI. Ligation of the linearized vector with meaBhcmA-hcmB was followed by transformation of *E. coli* DH5α (New England Biolabs, Frankfurt). The plasmid was checked by restriction and sequencing.

The vector pBBR1MCS-2::meaBhcmA-hcmB (FIG. 3, SEQ ID NO: 7) was introduced by means of electroporation (2.43 kV, 25 µF, 200Ω) into *R. eutropha* H16 PHB-4 (reclassified as *Cupriavidus necator*, DSM 541). By means of this method plasmid-harboring transformants were obtained.

5. Production of 2-hydroxyisobutyric Acid in Recombinant *R. eutropha* Cells To produce biomass, the plasmid-harboring *R. eutropha* strains described in examples 2 to 4 were grown in conical flasks containing 100 ml of biomass production medium (mod. MSM-Schlegel medium: 0.36% (w/v) $NH_2HPO_4$; 0.15% (w/v) $KH_2PO_4$; 0.1% (w/v) $NH_4Cl$; 1% (w/v) yeast extract, 0.8 mM $MgSO_4 \times 7\ H_2O$; 0.1 mM $CaCl_2 \times 2H_2O$; 37 µM $FeCl_3$; trace element solution (10×; Pfennig and Lippert, 1966), 0.1% (v/v)). The medium was additionally supplemented with 1.5% (w/v) fructose and 300 µg/ml kanamycin. Culturing was carried out in a shaker with temperature control at 30° C. and 180 rpm for approx. 18 h.

Nitrogen limitation was induced by removing the biomass by centrifugation (20° C.; max. 4000×g, 15 min) and then washing it in production medium (mod. MSM-Schlegel medium: 0.36% (w/v) $NH_2HPO_4$; 0.15% (w/v) $KH_2PO_4$; 0.8 mM $MgSO_4 \times 7H_2O$; 0.1 mM $CaCl_2 \times 2H_2O$; 37 µM $FeCl_3$; trace element solution (10×; Pfennig and Lippert, 1966), 0.1% (v/v)) and, after pelleting again, resuspending it in 50 ml of production medium. For production of 2-hydroxyisobutyric acid, the medium was also supplied with 76 nM $CoB_{12}$ in addition to 1.5% (w/v) fructose and 300 µg/ml kanamycin. Culturing was carried out at 30° C., 180 rpm for 6 hours, after which 1.5% (w/v) fructose and 76 nM coenzyme $B_{12}$ ($CoB_{12}$) were fed in again. The cells were harvested by centrifugation at 5000 rpm (4° C.) after 120 h, and the culture supernatant was stored at −20° C. until analysis.

Figure 3:
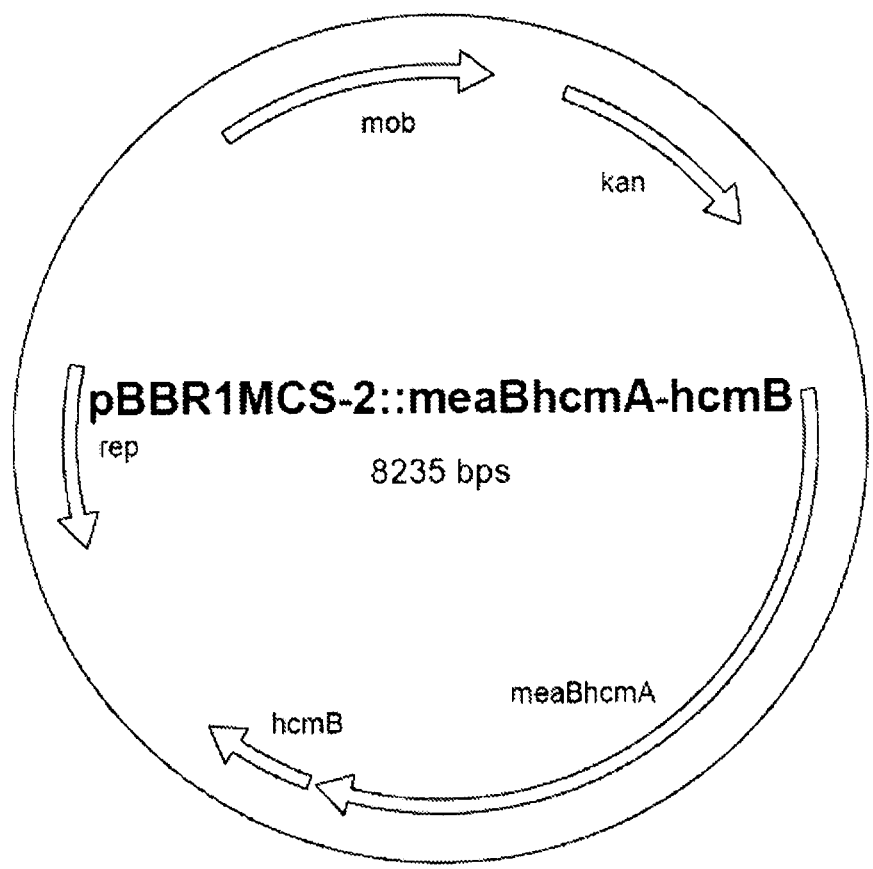
FIG. 3: Hybrid plasmid pBBR1MCS-2::meaBhcmA-hcmB.
Figure 4:
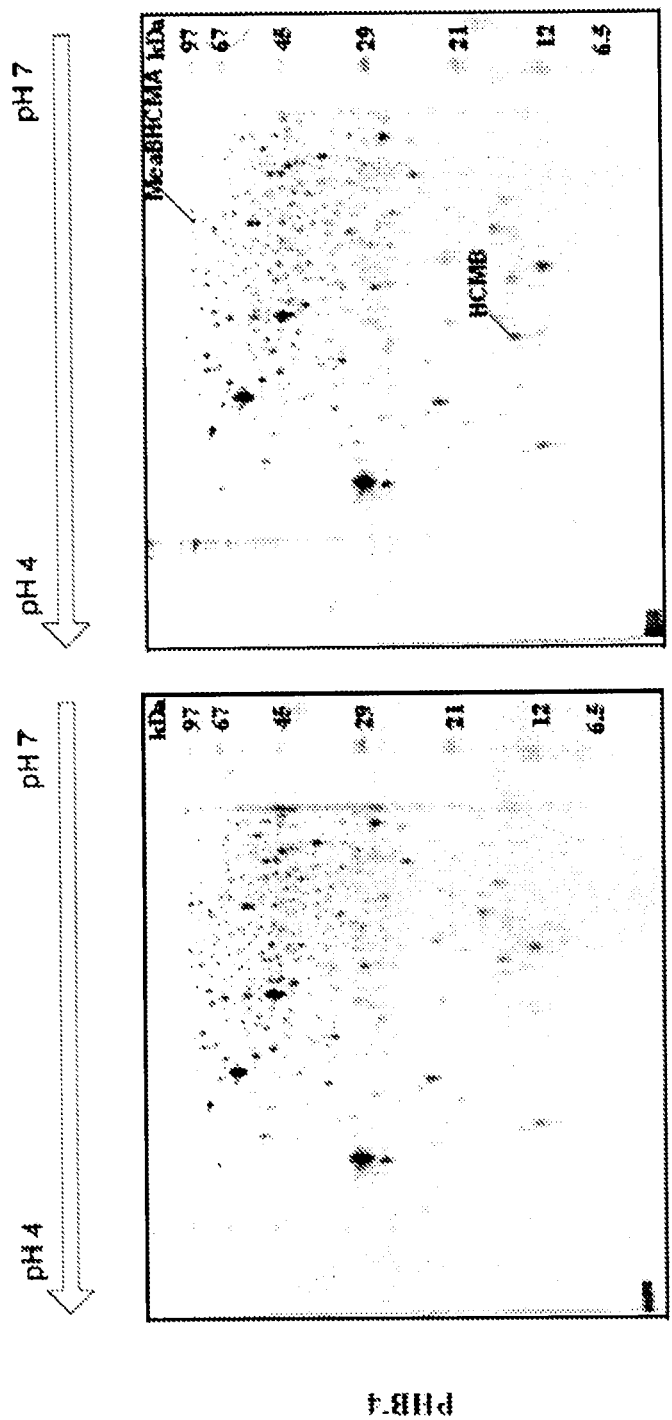
FIG. 4: 2D polyacrylamide gels (pH 4-pH 7) of the recombinant R. eutropha H16 PHB-4 strain.

Culture broth was removed during culturing in the production medium (see above) and spun down (13 000 rpm, 4° C.). The samples were then studied by means of IC, high performance liquid chromatography (HPLC) and quantitative $^1$H-NMR spectroscopy ($^1$H-NMR). In addition, 2 ml of the culture were harvested after 24 h in the production medium (see above) (13 000 rpm, 4° C.) The cell pellets were sent on dry ice to Toplab (Martinsried, Germany) and examined by 2D polyacrylamide gel electrophoresis. Both the MeaBhcmA fusion protein (98 kDa) and HcmB (14.5 kDa) were unambiguously identified by means of MS (FIG. 3).

Detection and quantification of 2-hydroxyisobutyric acid were carried out by means of IC, HPLC and $^1$H-NMR. Where appropriate, the culture supernatant was diluted with $_{dd}$H$_2$O for analysis by means of IC or HPLC. Chromatographic fractionation in the ICS-2000 RFIC (Dionex Corporation, Sunnyvale, USA) was carried out using the RFIC™ TonPac column (2×250 mm, column temperature: 30° C.+precolumn AG15 4×50 mm, flow rate 0.38 ml/min). HPLC (Agilent Technologies 1200 Series, Ratingen, Germany) made use of an Aminex column (HPX-87H, 300×7.8 mm) heated to 40° C. from Biorad (Hercules, USA; flow rate: 0.6 ml/min, max. 400 bar, injection volume: 20 µl). The 2-hydroxyisobutyric acid peak was identified by normalizing the retention time with the pure substance. The 2-hydroxyisobutyric acid content was estimated by spiking the samples with a defined amount of the pure substance, 2-hydroxy-isobutyric acid.

Figure 5:
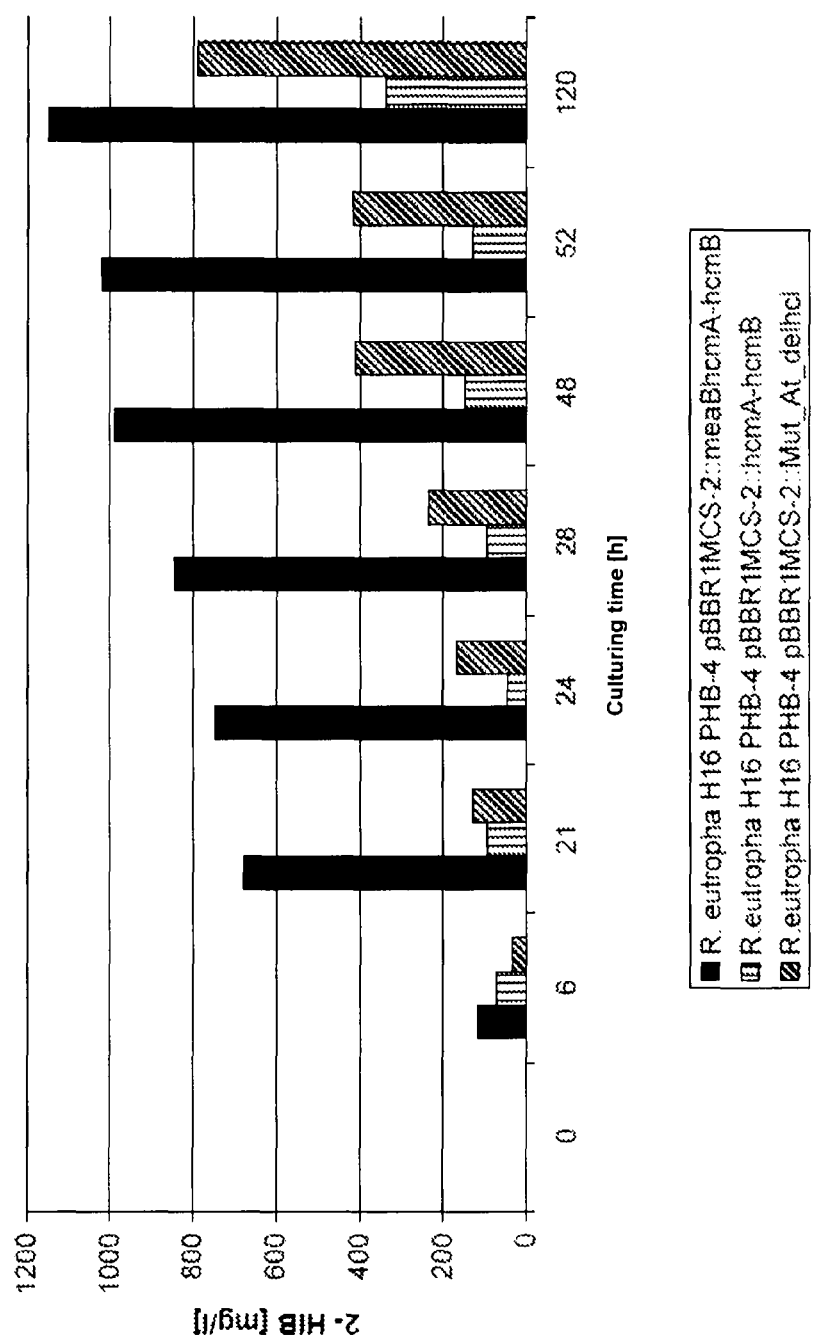
FIG. 5: Absolute 2-HIB concentration in the culture supernatant when culturing various recombinant R. eutropha H16 PHB-4 strains. Samples were taken after 6 h, 21 h, 24 h, 28 h, 48 h, 52 h and 120 h in the production medium and analyzed by means of ion exchange chromatography (IC).
Figure 6:
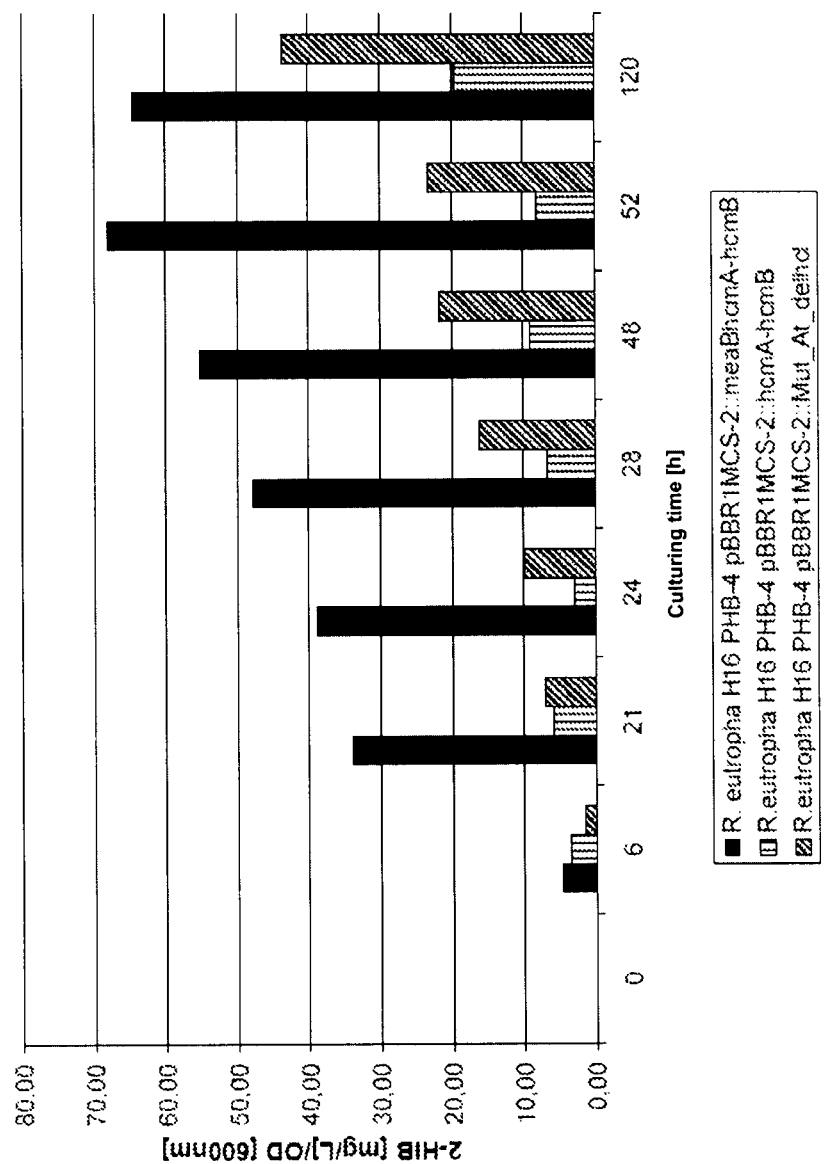
FIG. 6: 2-HIB concentration per $OD_{600}$ in the culture supernatant when culturing various recombinant R. eutropha H16 PHB-4 strains. Samples were taken after 6 h, 21 h, 24 h, 28 h, 48 h, 52 h and 120 h in the production medium and analyzed by means of IC.

A maximum concentration of 1.1 g/l (120 h in production medium) 2-hydroxyisobutyric acid was detected in the analyzed samples. This corresponds to a concentration of 64 mg/l/OD$_{600}$ (FIG. 5). In contrast, no 2-hydroxy-isobutyric acid was detected in corresponding control mixtures containing empty plasmid (pBBR1MCS-2). The IC measurements were confirmed qualitatively and quantitatively by adding the pure substance, 2-hydroxy-isobutyric acid.

The invention claimed is:

1. A fusion protein comprising (a) a protein having 3-hydroxycarboxylic acid-CoA mutase activity and comprising an amino acid sequence having at least 95% amino acid sequence identity to the amino acid sequence of SEQ ID NO: 21, 22, 28 or 29 fused to (b) a protein having ATPase/GTPase activity and comprising an amino acid sequence having at least 95% amino acid sequence identity to the amino acid sequence of SEQ ID NO: 1, 23, 24, 25, 26 or 27.

2. The fusion protein of claim 1, wherein (b) is N-terminally fused to (a).

3. The fusion protein of claim 1, wherein (b) is N-terminally fused to an amino acid sequence having at least 95% amino acid sequence identity to the amino acid sequence of SEQ ID NO: 22 or 29.

4. The fusion protein of claim 1, wherein
   the 3-hydroxycarboxylic acid-CoA mutase comprises the amino acid sequence of SEQ ID NO: 21 or 28,
   (b) is N terminally fused to the amino acid sequence of SEQ ID NO: 21 or 28,
   (b) comprises an amino acid sequence having at least 95% amino acid sequence identity to the amino acid sequence of SEQ ID NO: 1, and
   the fusion protein further comprises a linker consisting of the amino acid sequence Cys Ala Gly Ser Phe Pro Thr Ile (SEQ ID NO: 2) between (a) and (b).

5. The fusion protein of claim 1, wherein
   the 3-hydroxycarboxylic acid-CoA mutase comprises the amino acid sequence of SEQ ID NO: 21 or 28,
   (b) is N terminally fused to the amino acid sequence of SEQ ID NO: 21 or 28,
   (b) comprises the amino acid sequence of SEQ ID NO: 1, and
   the fusion protein further comprises a linker consisting of the amino acid sequence Cys Ala Gly Ser Phe Pro Thr Ile (SEQ ID NO: 2) between (a) and (b).

6. The fusion protein of claim 1, wherein the fusion protein comprises the amino acid sequences of SEQ ID NO: 3 and SEQ ID NO: 4 and wherein the fusion protein is heterodimeric.

7. The fusion protein of claim 1, wherein (b) comprises an amino acid sequence having at least 99% amino acid sequence identity to the amino acid sequence of SEQ ID NO: 1, 23, 24, 25, 26 or 27.

8. The fusion protein of claim 1, wherein (b) comprises the amino acid sequence of SEQ ID NO: 1, 23, 24, 25, 26 or 27.

9. A method of producing 2-hydroxyisobutyric acid, comprising contacting an aqueous medium comprising 3-hydroxybutyric acid with the fusion protein of claim 1 to produce 2-hydroxyisobutyric acid.

10. The method of claim 9, further comprising isolating the 2-hydroxyisobutyric acid.

11. The method of claim 9, wherein the aqueous medium comprises a microorganism expressing the fusion protein.

12. The method of claim 9, wherein the aqueous medium comprises a cell extract comprising the fusion protein.

13. A method of producing 2-hydroxyisobutyric acid, comprising contacting an aqueous medium comprising 3-hydroxybutyric acid with the fusion protein of claim 4 to produce 2-hydroxyisobutyric acid.

14. A method of producing 2-hydroxyisobutyric acid, comprising contacting an aqueous medium comprising 3-hydroxybutyric acid with the fusion protein of claim 5 to produce 2-hydroxyisobutyric acid.

15. A method for producing a methacrylic acid, methacrylic ester, or a polymer thereof, comprising:
   contacting an aqueous medium comprising 3-hydroxybutyric acid with the fusion protein of claim 1 to produce 2-hydroxyisobutyric acid,
   dehydrating the 2-hydroxyisobutyric acid to produce methacrylic acid,
   optionally, esterifying the methacrylic acid to produce methacrylic ester, and
   optionally, polymerizing the methacrylic ester to produce a polymer of methacrylic ester.

* * * * *